United States Patent
Rudolphi et al.

(10) Patent No.: US 8,518,998 B2
(45) Date of Patent: Aug. 27, 2013

(54) USE OF SULFONYL-SUBSTITUTED 2-SULFONYLAMINOBENZOIC ACID N-PHENYLAMIDES IN THE TREATMENT OF PAIN

(75) Inventors: Karl Rudolphi, Frankfurt am Main (DE); Martin Michaelis, Frankfurt (DE); Hans Guehring, Eltville (DE)

(73) Assignee: Sanofi-aventis Deutschland GmbH, Frankfurt am Main (DE)

( * ) Notice: Subject to any disclaimer, the term of this patent is extended or adjusted under 35 U.S.C. 154(b) by 466 days.

(21) Appl. No.: 12/749,986

(22) Filed: Mar. 30, 2010

(65) Prior Publication Data

US 2011/0021505 A1 Jan. 27, 2011

Related U.S. Application Data

(63) Continuation of application No. PCT/EP2008/007953, filed on Sep. 20, 2008.

(60) Provisional application No. 61/015,256, filed on Dec. 20, 2007.

(30) Foreign Application Priority Data

Oct. 5, 2007 (EP) .................................... 07019521
Jul. 31, 2008 (EP) .................................... 08013725

(51) Int. Cl.
*A01N 41/06* (2006.01)
*A61K 31/18* (2006.01)
*C07C 303/00* (2006.01)
*C07C 307/00* (2006.01)
*C07C 309/00* (2006.01)
*C07C 311/00* (2006.01)

(52) U.S. Cl.
USPC ........................................... 514/601; 564/80

(58) Field of Classification Search
USPC .......................................... 514/601; 564/80
See application file for complete search history.

(56) References Cited

U.S. PATENT DOCUMENTS

| | | | |
|---|---|---|---|
| 684,287 | A | 10/1901 | Millhiser et al. |
| 6,335,334 | B1 | 1/2002 | Schindler et al. |
| 6,881,735 | B2 | 4/2005 | Schindler et al. |
| 7,326,789 | B2 | 2/2008 | Schindler et al. |
| 8,106,213 | B2 | 1/2012 | Schindler et al. |
| 2003/0064992 | A1 | 4/2003 | Altmann et al. |
| 2004/0192680 | A1 | 9/2004 | Anderson et al. |
| 2009/0221573 | A1 | 9/2009 | Krahn et al. |
| 2012/0108573 | A1 | 5/2012 | Schindler et al. |

FOREIGN PATENT DOCUMENTS

| | | |
|---|---|---|
| DE | 10122894 | 11/2002 |
| WO | WO 00/02851 | 1/2000 |
| WO | 2007/003435 | 1/2007 |

OTHER PUBLICATIONS

Tesfaye et. al., Diabetologia, 2005, Springer-Verlag, vol. 48, pp. 805-807.*
International Search Report for WO2009/043495 dated Apr. 9, 2009.
Schindler, et al., Biochemistry and Pharmacology of Novel Anthranilic Acid Derivatives Activating Heme-Oxidized Soluble Guanylyl Cyclase, Molecular Pharmacoioay (2006, pp. 1260-1268, vol. 69).
Evgenov, et al., NO-independent stimulators and activators of soluble guanylate cyclase: discovery and therapeutic potential, Nature Reviews (2006, pp. 755-768, vol. 5).
Hargreaves, et al., A new and sensitive method for measuring thermal nociception in cutaneous hyperalgesia, Pain, (1988, pp. 77-88, vol. 32).
Guhring, et al., Suppressed Injury-Induced Rise in Spinal Prostaglandin E2 Production and Reduced Early Thermal Hyperalgesia in iNOS-Deficient Mice, The Journal of Neuroscience, (2000, pp. 6714-6720, vol. 18).
Tao, et al., Activation and Up-Regulation of Spinal Cord Nitric Oxide Receptor, Soluble Guanylate Cyclase, After Formalin Injection Into the Rat Hind Paw, Neuroscience, vol. 112, No. 2, pp. 439-446, (2002).
Tegeder, et al., Reduced Inflammatory Hyperalgesia With Preservation of Acute Thermal Nociception in Mice Lacking cGMP-Dependent Protein Kinase I, PNAS, (2004), vol. 101, No. 9, pp. 3253-3257.
Ferreira, et al., The Role of Systemic, Spinal and Supraspinal L-Arginine-Nitric Oxide-cGMP Pathway in Thermal Hyperalgesia Caused by intrathecal Injection of Glutamate in Mice, Neuropharmacology, vol. 38, (1999), pp. 835-842.
Schmidtko, et al., cGMP Produced by NO-Sensitive Guanylyl Cyclase Essentially Contributes to Inflammatory and Neuropathic Pain by Using Targets Different from cGMP-Dependent Protein Kinase I, The Journal of Neuroscience, (2008), vol. 28, No. 34, pp. 8568-8576.

* cited by examiner

*Primary Examiner* — Sreeni Padmanabhan
*Assistant Examiner* — Sarah Pihonak
(74) *Attorney, Agent, or Firm* — Jiang Lin

(57) ABSTRACT

The present invention relates to the use of sulfonyl-substituted 2-sulfonylaminobenzoic acid N-phenylamides of the formula I, wherein A and $R^1$ to $R^6$ have the meanings indicated in the claims, for treating pain and for manufacturing a medicament for the treatment of pain.

13 Claims, 2 Drawing Sheets

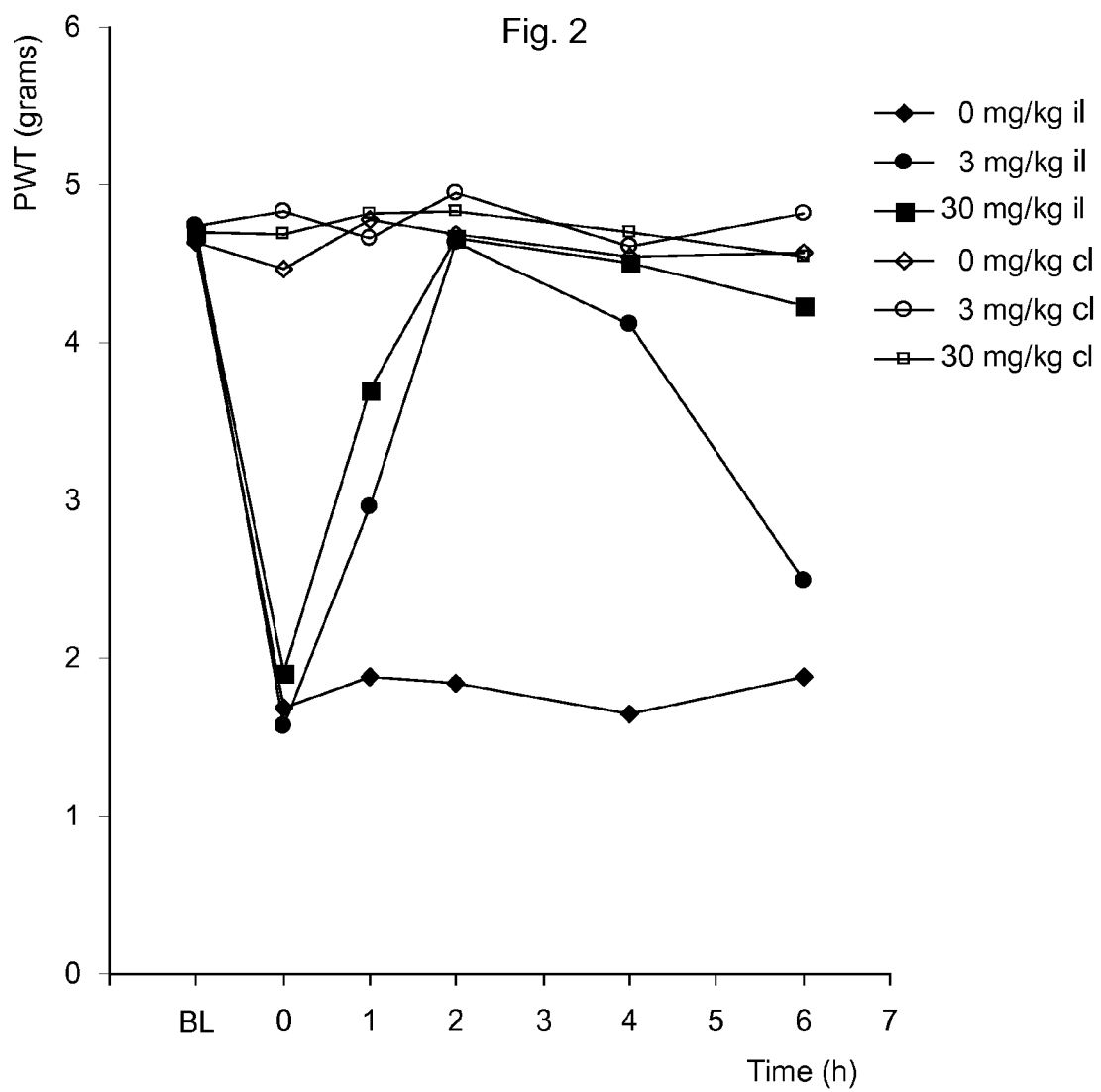

USE OF SULFONYL-SUBSTITUTED 2-SULFONYLAMINOBENZOIC ACID N-PHENYLAMIDES IN THE TREATMENT OF PAIN

The present invention relates to the use of sulfonyl-substituted 2-sulfonylaminobenzoic acid N-phenylamides of the formula I,

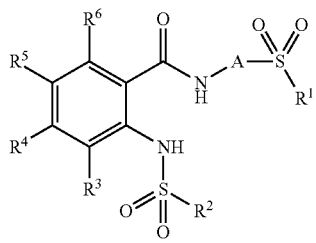

wherein A and $R^1$ to $R^6$ have the meanings indicated below, for treating pain and for manufacturing a medicament for the treatment of pain.

Pain, as defined by the International Association for the Study of Pain (IASP), is an unpleasant sensory and emotional experience associated with actual or potential tissue damage, or is described in terms of such damage. Pain can be acute pain or chronic pain. In particular in the case of acute pain, pain has a protective function for the body and is even vital to survival in that it prompts the organism to avoid a further exposure or re-exposure to the stimulus which caused the pain, for example a thermal or mechanical impact, or to seek for a cure of a dysfunction, and thus avoids further injury and tissue damage. However, apart from this beneficial aspect, pain generally puts a strain on the body and can be intolerable, and often needs to be alleviated by a suitable pain treatment in addition to treatment of the cause of the pain if the latter is possible. The necessity for pain treatment exists in particular in the case of chronic pain, for example in the case of neuropathic pain which is caused by a lesion or dysfunction in the nervous system, inflammatory pain or pain associated with cancer, in which case the cause of the pain often is not known or cannot be treated satisfactorily.

Pharmaceuticals belonging to a large number of different substance groups are employed for treating acute or chronic pain which have different modes of action and property profiles and act in the central nervous system or interfere with different parts of the nociceptive system. As examples, opioids, non-steroidal anti-inflammatory drugs, cyclooxygenase inhibitors and anticonvulsants and the specific compounds morphine, metamizol, carbamazepine, rofecoxib, ibuprofen and acetylsalicylic acid may be mentioned. Besides their analgesic activity, in part they exhibit other pharmacological activities such as an antiphlogistic or antipyretic action, for example, which provides an additional benefit. But despite the availability of a large number of analgesics, the treatment of pain has still not been satisfactorily solved, and there is an ongoing need for further potent analgesics which are well tolerated and exhibit a favorable property profile and can be used in the treatment of the various types of pain such as neuropathic pain or inflammatory pain, for example.

Surprisingly, it has now been found that the compounds of the formula I alleviate pain and can be used as analgesics in the treatment of pain. The compounds of the formula I have been described in WO 00/02851 and U.S. Pat. No. 6,335,334, for example, as activators of soluble guanylate cyclase which can be used in particular in the treatment of cardiovascular diseases such as atherosclerosis, hypertension, angina pectoris or cardiac insufficiency. An analgesic activity of the compounds of the formula I has not been described. Certain (thio)anthranilic acid N-arylamide derivatives, which inhibit VEGF (vascular endothelial growth factor) receptor tyrosine kinase activity and angiogenesis, and their use in the treatment of neoplastic diseases, retinopathy, age-related macular degeneration and other diseases such as inflammatory diseases or pain are described in US 2003/0064992. Data in support of an analgesic activity are not given in US 2003/0064992, and the specific structural features of the compounds of the present invention and their analgesic activity are neither anticipated nor suggested by US 2003/0064992.

Thus, a subject of the present invention is the use of a compound of the formula I,

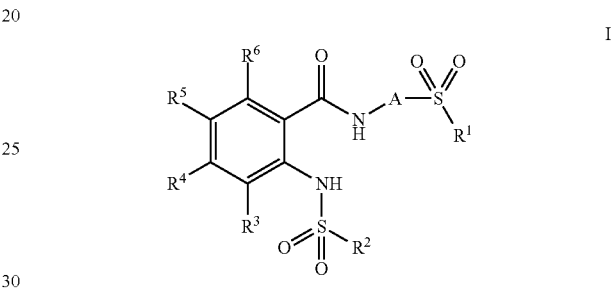

wherein
A is phenylene which can be substituted by one or more identical or different substituents chosen from halogen, ($C_1$-$C_4$)-alkyl and trifluoromethyl;
$R^1$ is chosen from $R^7R^8N$ and Het;
$R^2$ is phenyl or heteroaryl which can both be substituted by one or more identical or different substituents chosen from halogen, ($C_1$-$C_4$)-alkyl, trifluoromethyl, trifluoromethoxy, nitro, cyano, ($C_1$-$C_4$)-alkyl-O—, ($C_1$-$C_4$)-alkyl-CO—NH— and ($C_1$-$C_4$)-alkyl-S(O)$_2$—;
$R^3$, $R^4$, $R^5$ and $R^6$, which are independent of each other and can be identical or different, are chosen from hydrogen, halogen, ($C_1$-$C_4$)-alkyl, trifluoromethyl, cyano and ($C_1$-$C_4$)-alkyl-O—;
$R^7$ is chosen from hydrogen, ($C_1$-$C_4$)-alkyl and ($C_3$-$C_5$)-alkenyl;
$R^8$ is chosen from ($C_1$-$C_4$)-alkyl, ($C_1$-$C_4$)-alkyl-O—($C_1$-$C_4$)-alkyl-, di(($C_1$-$C_4$)-alkyl)N—($C_1$-$C_4$)-alkyl-, ($C_3$-$C_5$)-alkenyl, ($C_3$-$C_7$)-cycloalkyl, ($C_3$-$C_7$)-cycloalkyl-($C_1$-$C_4$)-alkyl-, phenyl-($C_1$-$C_4$)-alkyl-, indanyl and pyridinyl-($C_1$-$C_4$)-alkyl-, wherein cycloalkyl and pyridinyl can be substituted by one or more identical or different ($C_1$-$C_4$)-alkyl substituents;
heteroaryl is a residue of a monocyclic 5-membered or 6-membered aromatic heterocycle which contains one or two identical or different ring heteroatoms chosen from nitrogen, oxygen and sulfur;
Het is a residue of a monocyclic 5-membered, 6-membered or 7-membered saturated or partially unsaturated heterocycle which contains a ring nitrogen atom via which the group Het is bonded to the group -A-S(O)$_2$—, and which can contain one further ring heteroatom chosen from nitrogen, oxygen and sulfur wherein the sulfur atom can carry one or two oxo groups, and which can be substituted by one or more identical or different ($C_1$-$C_4$)-alkyl substituents, and to which a benzene ring can be fused wherein the benzene ring can be substituted by one or more identical or different substituents chosen from halogen, $(C_1-C_4)$-alkyl and trifluoromethyl; in any of its stereoisomeric forms, or a mixture of stereoisomeric forms in any ratio, or a physiologically acceptable salt thereof, for manufacturing a medicament for the treatment of pain.

Subjects of the invention also are a compound of the formula I as defined afore, in any of its stereoisomeric forms, or a mixture of stereoisomeric forms in any ratio, or a physiologically acceptable salt thereof, for use in the treatment of pain, a method of treating pain which comprises administering to a subject in need thereof a compound of the formula I as defined afore in any of its stereoisomeric forms, or a mixture of stereoisomeric forms in any ratio, or a physiologically acceptable salt thereof, as well as a pharmaceutical composition for use in the treatment of pain which comprises a compound of the formula I as defined afore in any of its stereoisomeric forms, or a mixture of stereoisomeric forms in any ratio, or a physiologically acceptable salt thereof, and a pharmaceutically acceptable carrier.

If groups or substituents can occur several times in the compounds of formula I such as, for example, alkyl substituents, they can all independently of one another have the indicated meanings and can in each case be identical or different.

Alkyl groups can be linear, i.e. straight-chain, or branched. This also applies when they are part of another group, for example an alkyl-O— group (alkoxy group) or substituted amino group, or when they are substituted, for example in the case of an $(C_1-C_4)$-alkyl-O—$(C_1-C_4)$-alkyl-, phenyl-$(C_1-C_4)$-alkyl- or $(C_3-C_7)$-cycloalkyl-$(C_1-C_4)$-alkyl- group. In substituted alkyl groups, the substituents can be present in any suitable positions. Examples of alkyl groups are methyl, ethyl, n-propyl, isopropyl, n-butyl, sec-butyl, isobutyl and tert-butyl. Examples of alkyl-O— groups are methoxy, ethoxy, n-propoxy, isopropoxy, n-butoxy, sec-butoxy, isobutoxy and tert-butoxy.

Alkenyl groups, i.e. unsaturated alkyl groups which comprise a double bond, can likewise be linear or branched. The double bond can be present in any position. In one embodiment of the invention, the carbon atom of an alkenyl group via which the group is bonded to the nitrogen atom in the group $R^7R^8N$, is not part of the double bond. Examples of alkenyl groups are prop-1-enyl, prop-2-enyl(allyl), but-2-enyl, 2-methyl-prop-2-enyl and 3-methyl-but-2-enyl.

Examples of cycloalkyl groups are cyclopropyl, cyclobutyl, cyclopentyl, cyclohexyl and cycloheptyl. Cycloalkyl groups, including cycloalkyl groups in cycloalkyl-alkyl-groups, can be unsubstituted or substituted by one or more, for example one, two, three or four, identical or different $(C_1-C_4)$-alkyl substituents, for example by methyl substituents, which can be present in any positions. In one embodiment of the invention, cycloalkyl groups are unsubstituted. Examples of substituted cycloalkyl groups are 4-methylcyclohexyl, 4-tert-butylcyclohexyl, 2,3-dimethylcyclopentyl and 3,5-dimethylcyclohexyl. Examples of cycloalkyl-alkyl-groups, which are bonded to the remainder of the molecule via the alkyl moiety as is symbolized by the terminal line (hyphen) next to the alkyl group which represents the free bond in the group cycloalkyl-alkyl- and generally in groups composed of subgroups, are cyclopropyl-methyl-, cyclobutyl-methyl-, cyclopentyl-methyl-, cyclohexyl-methyl-, cycloheptyl-methyl-, 1-cyclopropyl-ethyl-, 2-cyclopropyl-ethyl-, 2-cyclobutyl-ethyl-, 2-cyclopentyl-ethyl-, 2-cyclohexyl-ethyl- and 2-cycloheptyl-ethyl-.

Phenyl, heteroaryl, pyridinyl and phenylene groups can be unsubstituted or carry one or more, for example one, two, three or four, of the indicated substituents which can be identical or different and can be present in any positions. Besides that, in a pyridine ring, as well as in other suitable heterocycles, a ring nitrogen atom can carry an oxygen atom and the pyridine moiety be present in the form of a pyridine-N-oxide. In monosubstituted phenyl groups the substituent can be in the 2-position, the 3-position or the 4-position. In disubstituted phenyl groups the substituents can be in 2,3-position, 2,4-position, 2,5-position, 2,6-position, 3,4-position or 3,5-position. In trisubstituted phenyl residues the substituents can be in 2,3,4-position, 2,3,5-position, 2,3,6-position, 2,4,5-position, 2,4,6-position or 3,4,5-position. The free bonds in the divalent phenylene group representing the group A, via which it is bonded to the adjacent groups, can be present in any positions, and phenylene can thus be 1,2-phenylene (ortho-phenylene), 1,3-phenylene (meta-phenylene) and 1,4-phenylene (para-phenylene) which groups can all be unsubstituted or substituted as indicated. In case a phenyl group or any other group is substituted by nitro, the total number of nitro groups in a compound of the formula I preferably is not greater than two. Examples of phenyl groups which can occur in the compounds of the formula I and represent $R^2$, for example, are unsubstituted phenyl, 2-fluoro-phenyl, 3-fluoro-phenyl, 4-fluoro-phenyl, 2-chloro-phenyl, 3-chloro-phenyl, 4-chloro-phenyl, 2-bromo-phenyl, 3-bromo-phenyl, 4-bromo-phenyl, 2-methyl-phenyl(o-tolyl), 3-methyl-phenyl (m-tolyl), 4-methyl-phenyl(p-tolyl), 2-trifluoromethyl-phenyl, 3-trifluoromethyl-phenyl, 4-trifluoromethyl-phenyl, 2-methoxy-phenyl, 3-methoxy-phenyl, 4-methoxy-phenyl, 2-trifluoromethoxy-phenyl, 3-trifluoromethoxy-phenyl, 4-trifluoromethoxy-phenyl, 2-acetylamino-phenyl, 3-acetylamino-phenyl, 4-acetylamino-phenyl, 2-cyano-phenyl, 3-cyano-phenyl, 4-cyano-phenyl, 2,3-difluoro-phenyl, 2,4-difluoro-phenyl, 2,5-difluoro-phenyl, 2,6-difluoro-phenyl, 3,4-difluoro-phenyl, 3,5-difluoro-phenyl, 2,3-dichloro-phenyl, 2,4-dichloro-phenyl, 2,5-dichloro-phenyl, 2,6-dichloro-phenyl, 3,4-dichloro-phenyl, 3,5-dichloro-phenyl, 2-chloro-3-fluoro-phenyl, 2-chloro-4-fluoro-phenyl, 2-chloro-5-fluoro-phenyl, 2-chloro-6-fluoro-phenyl, 3-chloro-2-fluoro-phenyl, 3-chloro-4-fluoro-phenyl, 3-chloro-5-fluoro-phenyl, 4-chloro-2-fluoro-phenyl, 4-chloro-3-fluoro-phenyl, 5-chloro-2-fluoro-phenyl, 2,3-dimethyl-phenyl, 2,4-dimethyl-phenyl, 2,5-dimethyl-phenyl, 2,6-dimethyl-phenyl, 3,4-dimethyl-phenyl, 3,5-dimethyl-phenyl, 2,3-dimethoxy-phenyl, 2,4-dimethoxy-phenyl, 2,5-dimethoxy-phenyl, 2,6-dimethoxy-phenyl, 3,4-dimethoxy-phenyl and 3,5-dimethoxy-phenyl.

A heteroaryl group representing the group $R^2$ is preferably a residue of a 5-membered aromatic heterocycle which comprises one ring heteroatom chosen from nitrogen, oxygen and sulfur or two ring heteroatoms one of which is a nitrogen atom and the other of which is chosen from nitrogen, oxygen and sulfur, or a residue of a 6-membered aromatic heterocycle which comprises one or two ring nitrogen atoms. The ring heteroatoms can be present in any suitable positions. Examples of heteroaryl groups are pyrrolyl (1H-pyrrolyl), furanyl, thiophenyl(thienyl), imidazolyl (1H-imidazolyl), pyrazolyl (1H-pyrazolyl), oxazolyl (1,3-oxazolyl), isoxazolyl (1,2-oxazolyl), thiazolyl (1,3-thiazolyl), isothiazolyl (1,2-thiazolyl), pyridinyl(pyridyl), pyridazinyl, pyrimidinyl and pyrazinyl, which can all be substituted as indicated. A heteroaryl group representing the group $R^2$ is preferably bonded to the sulfur atom in the group $R^2$—$S(O)_2$— via a ring carbon atom which ring carbon atom can be present in any position. For example, a furyl group can be furan-2-yl (2-furyl) or furan-3-yl (3-furyl), a thiophenyl(thienyl) group can be thiophen-2-yl (2-thienyl) or thiophen-3-yl (3-thienyl), an imidazolyl group can be imidazol-2-yl, imidazol-4-yl or imidazol-5-yl, a thiazolyl group can be thiazol-2-yl, thiazol-4-yl or thiazol-5-yl, an isoxazolyl group can be isoxazol-3-yl, isoxazol-4-yl or isoxazol-5-yl, a pyridinyl group can be pyridin-2-yl (2-pyridyl), pyridin-3-yl (3-pyridyl) or pyridin-4-yl (4-pyridyl). The substituents in substituted heteroaryl groups can be present in any positions. For example, in a furan-2-yl group and thiophen-2-yl group substituents can be present in the 3-position and/or 4-position and/or 5-position, in a furan-3-yl group and thiophen-3-yl group in the 2-position and/or 4-position and/or 5-position, in an imidazol-2-yl group in the 1-position and/or 4-position and/or 5-position, in an imidazol-4-yl group in the 1-position and/or 2-position and/or 5-position, in an imidazol-5-yl group in the 1-position and/or 2-position and/or 4-position, in a thiazol-2-yl group in the 4-position and/or 5-position, in a thiazol-4-yl group in the 2-position and/or 5-position, in a thiazol-5-yl group in the 2-position and/or 4-position, in an isoxazol-3-yl group in the 4-position and/or 5-position, in an isoxazol-4-yl group in the 3-position and/or 5-position, in an isoxazol-5-yl group in the 3-position and/or 4-position, in a pyridin-2-yl group in the 3-position and/or 4-position and/or 5-position and/or 6-position, in a pyridin-3-yl group in the 2-position and/or 4-position and/or 5-position and/or 6-position, in a pyridin-4-yl group in the 2-position and/or 3-position and/or 5-position and/or 6-position. In case a heteroaryl group comprises a ring nitrogen atom which carries a hydrogen atom or a substituent, such as in the case of a pyrrolyl, imidazolyl or pyrazolyl group, in one embodiment of the invention, the substituent on such a ring nitrogen atom is chosen from $(C_1-C_4)$-alkyl and $CF_3$, in particular from $(C_1-C_4)$-alkyl, and the substituents on ring carbon atoms are as indicated. Examples of heteroaryl groups which can occur in the compounds of the formula I and represent $R^2$, are thiophen-2-yl, thiophen-3-yl, 3-chloro-thiophen-2-yl, 4-chloro-thiophen-2-yl, 5-chloro-thiophen-2-yl, 2-chloro-thiophen-3-yl, 4-chloro-thiophen-3-yl, 5-chloro-thiophen-3-yl, 3,4-dichloro-thiophen-2-yl, 3,5-dichloro-thiophen-2-yl, 4,5-dichloro-thiophen-2-yl, 2,4-dichloro-thiophen-3-yl, 2,5-dichloro-thiophen-3-yl, 4,5-dichloro-thiophen-3-yl, 5-chloro-1,3-dimethyl-pyrazol-4-yl, 1-methyl-imidazol-4-yl, 2,4-dimethyl-thiazol-5-yl, 2-acetylamino-4-methyl-thiazol-5-yl, 3,5-dimethyl-isoxazol-4-yl, pyridin-2-yl, pyridin-3-yl and pyridin-4-yl.

Examples of phenyl-$(C_1-C_4)$-alkyl- groups are benzyl, 1-phenyl-ethyl- and 2-phenyl-ethyl-. Examples of pyridinyl-$(C_1-C_4)$-alkyl- groups are pyridinyl-methyl-, 1-pyridinyl-ethyl- and 2-pyridinyl-ethyl-, wherein the pyridinyl group can be pyridin-2-yl, pyridin-3-yl and pyridin-4-yl. Examples of indanyl groups, which are preferably bonded via a carbon atom in the 5-membered ring, are indan-1-yl and indan-2-yl.

In case a group Het representing $R^1$, which group is bonded to the sulfur atom in the group -A-S(O)$_2$— via a ring nitrogen atom, is a residue of a partially unsaturated heterocycle, it is non-aromatic and contains one or two double bonds, preferably one double bond, within the ring which double bonds can be present in any positions. In case a benzene ring is fused to the heterocycle, a double bond is common to both the heterocyclic ring and the benzene ring. The further ring heteroatom which can be present in the group Het in addition to the ring nitrogen atom via which Het is bonded, can be present in any position. In one embodiment of the invention, the further ring heteroatom is present in a position which is not adjacent to the ring nitrogen atom via which the group Het is bonded, i.e., the further ring heteroatom is separated from the ring nitrogen atom via which Het is bonded by at least one ring carbon atom, for example by two ring carbon atoms. In the group Het one or more, for example one, two, three, four or five, identical or different $(C_1-C_4)$-alkyl substituents, for example methyl substituents, can be present in any positions, independently of one another on all ring carbon atoms and/or on a further ring nitrogen atom. If a sulfur atom is present as further ring heteroatom, it can carry one or two oxo groups (=O), i.e. it can be present in the form of a sulfoxide group —S(O)— or a sulfone group —S(O)$_2$—. A benzene ring which can be fused to the heterocyclic ring in the group Het, can be unsubstituted or substituted by one or more, for example one, two, three or four identical or different substituents as indicated which can be present in any positions. In one embodiment of the invention, the benzene ring which can be fused to the heterocyclic ring, is unsubstituted. Examples of the group Het are pyrrolidin-1-yl(pyrrolidino), 2,5-dihydro-1H-pyrrol-1-yl, 2,3-dihydro-1H-isoindol-2-yl, pyrazolidin-1-yl, imidazolidin-1-yl, oxazolidin-3-yl (1,3-oxazolidin-3-yl), thiazolidin-3-yl (1,3-thiazolidin-3-yl), piperidin-1-yl (piperidino), 1,2,3,4-tetrahydropyridin-1-yl, 1,2,3,6-tetrahydropyridin-1-yl, 1,2,3,4-tetrahydroquinolin-1-yl, 1,2,3,4-tetrahydroisoquinolin-2-yl, perhydropyrimidin-1-yl, 1,4,5,6-tetrahydropyrimidin-1-yl, piperazin-1-yl, perhydro-1,3-oxazin-3-yl, morpholin-4-yl(morpholino), perhydro-1,3-thiazin-3-yl, thiomorpholin-4-yl(thiomorpholino), perhydroazepin-1-yl, perhydro-1,4-diazepin-1-yl(homopiperazin-1-yl) and perhydro-1,4-oxazepin-4-yl, which can all be unsubstituted or substituted by alkyl substituents on one or more ring carbon atoms and/or on the ring nitrogen atom via which the group is not bonded to the group -A-S(O)$_2$—, and/or which can carry on the ring sulfur atom one or two oxo group, and thus can also occur in the compounds of the formula I in the form of a group such as 2-methyl-piperidin-1-yl, 3-methyl-piperidin-1-yl, 4-methyl-piperidin-1-yl, 2,6-dimethyl-piperidin-1-yl, cis-2,6-dimethyl-piperidin-1-yl, 3,5-dimethyl-piperidin-1-yl, cis-3,5-dimethyl-piperidin-1-yl, 4-methyl-piperazin-1-yl, 4-ethyl-piperazin-1-yl, 2,6-dimethyl-morpholin-4-yl, cis-2,6-dimethyl-morpholin-4-yl, 3,5-dimethyl-morpholin-4-yl, cis-3,5-dimethyl-morpholin-4-yl, 1-oxo-thiomorpholin-4-yl, 1,1-dioxo-thiomorpholin-4-yl or 4-methyl-perhydro-1,4-diazepin-1-yl, for example.

Halogen is fluorine, chlorine, bromine oder iodine, preferably fluorine, chlorine or bromine, more preferably fluorine or chlorine.

The present invention includes all stereoisomeric forms of the compounds of the formula I. Centers of asymmetry that are present in the compounds of formula I can all independently of one another have S configuration or R configuration. The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism, the invention includes both the cis form and the trans form as well as mixtures of these forms in all ratios. If desired, the preparation of individual stereoisomers can be carried out by separation of a mixture of isomers by customary methods, for example by chromatography or crystallization, by the use of stereochemically uniform starting materials for the synthesis, or by stereoselective synthesis. Optionally a derivatization can be carried out before a separation of stereoisomers. The separation of a mixture of stereoisomers can be carried out at the stage of the compounds of the formula I or at the stage of an intermediate during the synthesis. The invention also includes all tautomeric forms of the compounds of formula I.

If the compounds of the formula I contain one or more acidic or basic groups, the invention also includes the corresponding physiologically or toxicologically acceptable salts, in particular the pharmaceutically utilizable salts. Thus, the compounds of the formula I which contain acidic groups can be present on these groups and can be used according to the invention as alkali metal salts, alkaline earth metal salts or as ammonium salts, for example. Examples of such salts are sodium salts, potassium salts, calcium salts, magnesium salts or salts with ammonia or organic amines such as, for example, ethylamine, ethanolamine, triethanolamine or amino acids. Compounds of the formula I which contain one or more basic groups, i.e. groups which can be protonated, can be present and can be used according to the invention in the form of their acid addition salts with inorganic or organic acids, for example as salts with hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid or adipic acid. If the compounds of the formula I simultaneously contain acidic and basic groups in the molecule, the invention also includes, in addition to the salt forms mentioned, inner salts or betaines (zwitterions). Salts can be obtained from the compounds of the formula I by customary methods which are known to the person skilled in the art, for example by combination with an organic or inorganic acid or base in a solvent, or by anion exchange or cation exchange from other salts. The present invention furthermore includes all physiologically acceptable solvates of the compounds of the formula I, for example hydrates or adducts with alcohols, and also derivatives, prodrugs and active metabolites of the compounds of the formula I.

If the group A is substituted, i.e. if it carries one or more further substituents in addition to the group $R^1—S(O)_2—$ and the carboxamide group depicted in formula I, it is preferably substituted by one or two identical or different substituents chosen from the indicated substituents, for example by one substituent. Preferably, the substituents on a phenylene group representing A are chosen from halogen and $(C_1-C_4)$-alkyl, more preferably from fluorine, chlorine and $(C_1-C_4)$-alkyl, particularly preferably from fluorine, chlorine and methyl. In one embodiment of the invention substituents on a phenylene group representing A are chosen from $(C_1-C_4)$-alkyl, and in particular are methyl substituents. In one embodiment of the invention a phenylene group representing A is unsubstituted, i.e. besides the group $R^1—S(O)_2—$ and the carboxamide group depicted in formula I it carries four hydrogen atoms. Preferably, the phenylene group representing A is 1,3-phenylene or 1,4-phenylene, more preferably 1,4-phenylene, which can all be unsubstituted or substituted as mentioned. In one embodiment of the invention A is unsubstituted 1,4-phenylene.

In one embodiment of the invention, $R^1$ is $R^7R^8N$. In another embodiment of the invention, $R^1$ is Het.

$R^2$ is preferably phenyl or heteroaryl which can both be substituted by one, two or three, preferably by one or two, identical or different substituents. The substituents on $R^2$ are preferably chosen from halogen, $(C_1-C_4)$-alkyl, trifluoromethyl, cyano, $(C_1-C_4)$-alkyl-O— and $(C_1-C_4)$-alkyl-CO—NH—, more preferably from halogen, $(C_1-C_4)$-alkyl, trifluoromethyl and $(C_1-C_4)$-alkyl-O—, particularly preferably from halogen, $(C_1-C_4)$-alkyl and trifluoromethyl, more particularly preferably from halogen and $(C_1-C_4)$-alkyl, especially preferably from fluorine, chlorine and $(C_1-C_4)$-alkyl, more especially preferably from chlorine and $(C_1-C_4)$-alkyl, for example from chlorine and methyl. In one embodiment of the invention, $R^2$ is phenyl or heteroaryl which can both be substituted by one or two identical or different halogen atoms, preferably fluorine and/or chorine atoms. In another embodiment of the invention, $R^2$ is phenyl or heteroaryl which can both be substituted by one or two chlorine atoms. In one embodiment of the invention, $R^2$ is phenyl which can be substituted in any of the mentioned ways and preferably is substituted in any of the mentioned ways. In another embodiment of the invention, $R^2$ is heteroaryl which can be substituted in any of the mentioned ways and preferably is substituted in any of the mentioned ways.

$R^3$, $R^4$, $R^5$ and $R^6$ are preferably chosen from hydrogen, halogen, $(C_1-C_4)$-alkyl and $(C_1-C_4)$-alkyl-O—, more preferably from hydrogen, halogen and $(C_1-C_4)$-alkyl-O—, particularly preferably from hydrogen and halogen, wherein halogen representing $R^3$, $R^4$, $R^5$ and $R^6$ preferably is fluorine or chlorine, more preferably chlorine. $(C_1-C_4)$-Alkyl representing $R^3$, $R^4$, $R^5$ and $R^6$ preferably is methyl, and $(C_1-C_4)$-alkyl-O— representing $R^3$, $R^4$, $R^5$ and $R^6$ preferably is methoxy. Preferably, two of the groups $R^3$, $R^4$, $R^5$ and $R^6$ are hydrogen and the others of the groups $R^3$, $R^4$, $R^5$ and $R^6$, which can be identical or different, can have any of the indicated meanings including hydrogen. In one embodiment of the invention, at least one of the groups $R^3$, $R^4$, $R^5$ and $R^6$ is not hydrogen and the others of the groups $R^3$, $R^4$, $R^5$ and $R^6$, which can be identical or different, can have any of the indicated meanings including hydrogen, i.e., in this embodiment the benzene ring carrying $R^3$, $R^4$, $R^5$ and $R^6$ which is depicted in formula I, is substituted by at least one substituent. In one embodiment of the invention, one or two of the groups $R^3$, $R^4$, $R^5$ and $R^6$, for example one of the groups $R^3$, $R^4$, $R^5$ and $R^6$, are not hydrogen and thus are independently of each other chosen from halogen, $(C_1-C_4)$-alkyl, trifluoromethyl, cyano and $(C_1-C_4)$-alkyl-O— or from the groups comprised by any of the preferred definitions of $R^3$, $R^4$, $R^5$ and $R^6$ which are different from hydrogen, and the others of the groups $R^3$, $R^4$, $R^5$ and $R^6$ are hydrogen. If one or two of the groups $R^3$, $R^4$, $R^5$ and $R^6$ are not hydrogen, these groups can be either the group $R^3$ only, or the group $R^4$ only, or the group $R^5$ only, or the group $R^6$ only, or the groups $R^3$ and $R^4$, or the groups $R^3$ and $R^5$, or the groups $R^3$ and $R^6$, or the groups $R^4$ and $R^5$, or the groups $R^4$ and $R^6$, or the groups $R^5$ and $R^6$, the others of the groups $R^3$, $R^4$, $R^5$ and $R^6$ then being hydrogen. If one or two of the groups $R^3$, $R^4$, $R^5$ and $R^6$ are not hydrogen, these groups preferably are either the group $R^4$ only, or the group $R^5$ only, or the group $R^6$ only, or the groups $R^4$ and $R^5$, or the groups $R^4$ and $R^6$, or the groups $R^5$ and $R^6$, more preferably either the group $R^4$ only, or the group $R^5$ only, or the group $R^6$ only, or the groups $R^4$ and $R^5$, or the groups $R^5$ and $R^6$, particularly preferably either the group $R^4$ only, or the group $R^5$ only, or the groups $R^4$ and $R^5$, more particularly preferably either the group $R^5$ only or the groups $R^4$ and $R^5$, the others of the groups $R^3$, $R^4$, $R^5$ and $R^6$ then being hydrogen. In one embodiment of the invention, $R^5$ is different from hydrogen and is chosen from halogen, $(C_1-C_4)$-alkyl, trifluoromethyl, cyano and $(C_1-C_4)$-alkyl-O—, preferably from halogen, $(C_1-C_4)$-alkyl and $(C_1-C_4)$-alkyl-O—, more preferably from halogen and $(C_1-C_4)$-alkyl-O—, particularly preferably from halogen, $R^4$ is chosen from hydrogen, halogen, $(C_1-C_4)$-alkyl, trifluoromethyl, cyano and $(C_1-C_4)$-alkyl-O—, preferably from hydrogen, halogen, $(C_1-C_4)$-alkyl and $(C_1-C_4)$-alkyl-O—, more preferably from hydrogen, halogen and $(C_1-C_4)$-alkyl-O—, particularly preferably from hydrogen and $(C_1-C_4)$-alkyl-O—, and $R^3$ and $R^6$ are hydrogen, wherein halogen representing $R^4$ and/or $R^5$ preferably is fluorine or chlorine, more preferably chlorine, $(C_1-C_4)$-alkyl representing $R^4$ and/or $R^5$ preferably methyl, and $(C_1-C_4)$-alkyl-O— representing $R^4$ and/or $R^5$ preferably is methoxy. In another embodiment of the invention, one or two of the groups $R^4$ and $R^5$ are independently of each other chosen from hydrogen, chlorine and methoxy and the others of the substituents $R^3$, $R^4$, $R^5$ and $R^6$ are hydrogen, wherein at least one of the groups $R^3$, $R^4$, $R^5$ and $R^6$ is different from hydrogen. In another embodiment of the invention, $R^5$ is chlorine and $R^3$, $R^4$ and $R^6$ are hydrogen. In another embodiment of the invention, $R^4$ and $R^5$ are methoxy and $R^3$ and $R^6$ are hydrogen.

$R^7$ is preferably chosen from hydrogen and $(C_1-C_4)$-alkyl, more preferably from hydrogen and methyl. In one embodiment of the invention, $R^7$ is hydrogen. In another embodiment of the invention, $R^7$ is chosen from $(C_1-C_4)$-alkyl and $(C_3-C_5)$-alkenyl, preferably from $(C_1-C_4)$-alkyl, and can be methyl, for example.

$R^8$ is preferably chosen from $(C_1-C_4)$-alkyl, $(C_1-C_4)$-alkyl-O—$(C_1-C_4)$-alkyl-, di$((C_1-C_4)$-alkyl$)$N—$(C_1-C_4)$-alkyl-, $(C_3-C_7)$-cycloalkyl, phenyl-$(C_1-C_4)$-alkyl-, indanyl and pyridinyl-$(C_1-C_4)$-alkyl-, more preferably from $(C_1-C_4)$-alkyl, $(C_3-C_7)$-cycloalkyl, phenyl-$(C_1-C_4)$-alkyl- and pyridinyl-$(C_1-C_4)$-alkyl-, particularly preferably from $(C_1-C_4)$-alkyl, $(C_3-C_7)$-cycloalkyl and pyridinyl-$(C_1-C_4)$-alkyl-, wherein cycloalkyl and pyridinyl can be substituted as indicated.

In one embodiment of the invention, the group heteroaryl group representing the group $R^2$ is residue of a 5-membered aromatic heterocycle which comprises one ring heteroatom chosen from nitrogen, oxygen and sulfur or two ring heteroatoms one of which is a nitrogen atom and the other of which is chosen from nitrogen, oxygen and sulfur, which can be substituted as indicated with respect to the group $R^2$. In another embodiment of the invention, the group heteroaryl is the group thiophenyl (thienyl) or a residue of a 5-membered aromatic heterocycle which comprises a ring nitrogen atom and one further ring heteroatom chosen from nitrogen, oxygen and sulfur, which can all be substituted as indicated with respect to the group $R^2$. In another embodiment of the invention, the group heteroaryl is chosen from thiophenyl (thienyl), pyrazolyl, imidazolyl, oxazolyl, isoxazolyl and thiazolyl, preferably from thiophenyl(thienyl), oxazolyl, isoxazolyl and thiazolyl, more preferably from thiophenyl(thienyl), isoxazolyl and thiazolyl, particularly preferably from thiophenyl (thienyl) and isoxazolyl, which can all be substituted as indicated with respect to the group $R^2$. In one embodiment of the invention, $R^2$ is thiophenyl(thienyl) which can be substituted as indicated with respect to the group $R^2$, for example by chlorine and/or methyl, in particular by chlorine, and can be thiophen-2-yl (2-thienyl) or thiophen-3-yl (3-thienyl), in particular thiophen-2-yl. In another embodiment of the invention, $R^2$ is isoxazolyl which can be substituted as indicated with respect to the group $R^2$, for example by chlorine and/or methyl, in particular by methyl, and can be isoxazol-3-yl or isoxazol-4-yl or isoxazol-5-yl, in particular isoxazol-4-yl. In another embodiment of the invention, $R^2$ is thiazolyl which can be substituted as indicated with respect to the group $R^2$, for example by chlorine and/or methyl, in particular by methyl, and can be thiazol-2-yl or thiazol-4-yl or thiazol-5-yl, in particular thiazol-5-yl.

In one embodiment of the invention, Het is a residue of a monocyclic 5-membered, 6-membered or 7-membered heterocycle which is saturated or contains one double bond within the ring and contains a ring nitrogen atom via which the group Het is bonded to the group -A-S(O)$_2$—, and which can contain one further ring heteroatom chosen from nitrogen, oxygen and sulfur wherein the sulfur atom can carry one or two oxo groups, and which can be substituted by one or more identical or different $(C_1-C_4)$-alkyl substituents, and to which a benzene ring can be fused wherein the benzene ring can be substituted by one or more identical or different substituents chosen from halogen, $(C_1-C_4)$-alkyl and trifluoromethyl. In another embodiment of the invention, Het is a residue of a monocyclic 5-membered, 6-membered or 7-membered heterocycle which contains one double bond within the ring and contains a ring nitrogen atom via which the group Het is bonded to the group -A-S(O)$_2$—, and which can contain one further ring heteroatom chosen from nitrogen, oxygen and sulfur wherein the sulfur atom can carry one or two oxo groups, and which can be substituted by one or more identical or different $(C_1-C_4)$-alkyl substituents, and to which a benzene ring can be fused wherein the benzene ring can be substituted by one or more identical or different substituents chosen from halogen, $(C_1-C_4)$-alkyl and trifluoromethyl. In another embodiment of the invention, Het is a residue of a monocyclic 5-membered, 6-membered or 7-membered heterocycle which contains one double bond within the ring and contains a ring nitrogen atom via which the group Het is bonded to the group -A-S(O)$_2$—, and which can contain one further ring heteroatom chosen from nitrogen, oxygen and sulfur wherein the sulfur atom can carry one or two oxo groups, and which can be substituted by one or more identical or different $(C_1-C_4)$-alkyl substituents, and to which a benzene ring is fused wherein the benzene ring can be substituted by one or more identical or different substituents chosen from halogen, $(C_1-C_4)$-alkyl and trifluoromethyl. In another embodiment of the invention, Het is a residue of a monocyclic 5-membered, 6-membered or 7-membered heterocycle which is saturated and contains a ring nitrogen atom via which the group Het is bonded to the group -A-S(O)$_2$—, and which can contain one further ring heteroatom chosen from nitrogen, oxygen and sulfur wherein the sulfur atom can carry one or two oxo groups, and which can be substituted by one or more identical or different $(C_1-C_4)$-alkyl substituents. Preferably, Het is a residue of a 5-membered or 6-membered heterocycle as specified, more preferably a residue of a 6-membered heterocycle as specified. The further ring heteroatom which can be present in Het, is preferably chosen from oxygen and sulfur wherein the sulfur atom can carry one or two oxo groups, and more preferably is oxygen. In one embodiment of the invention, the group Het contains a further ring heteroatom which is chosen from nitrogen, oxygen and sulfur, and preferably is chosen from oxygen and sulfur and more preferably is oxygen, in addition to the nitrogen atom via which the group Het is bonded to the group -A-S(O)$_2$—, wherein the sulfur atom can carry one or two oxo groups. In another embodiment of the invention, the group Het does not contain a further ring heteroatom in addition to the nitrogen atom via which the group Het is bonded to the group -A-S(O)$_2$—. The number of alkyl substituents which can be present in the group Het, is preferably one, two, three or four, more preferably one, two or three, for example one or two. Alkyl substituents which are present in Het, are preferably methyl groups. In one embodiment of the invention, the group Het is not substituted by alkyl substituents. In another embodiment of the invention, the group Het is substituted by alkyl substituents in any of the mentioned ways. In one embodiment of the invention, Het is chosen from pyrrolidin-1-yl, oxazolidin-3-yl, thiazolidin-3-yl, piperidin-1-yl, 1,2,3,4-tetrahydroisoquinolin-2-yl, piperazin-1-yl, morpholin-4-yl, thiomorpholin-4-yl and perhydroazepin-1-yl, preferably from pyrrolidin-1-yl, piperidin-1-yl, 1,2,3,4-tetrahydroisoquinolin-2-yl, piperazin-1-yl, morpholin-4-yl and thiomorpholin-4-yl, more preferably from piperidin-1-yl, 1,2,3,4-tetrahydroisoquinolin-2-yl, morpholin-4-yl and thiomorpholin-4-yl, particularly preferably from morpholin-4-yl and thiomorpholin-4-yl, which can all be unsubstituted or substituted by alkyl substituents in any of the mentioned ways and thus can also occur in the compounds of the formula I in the form of a group such as 2,6-dimethyl-piperidin-1-yl, cis-2,6-dimethyl-piperidin-1-yl, 3,5-dimethyl-piperidin-1-yl, cis-3,5-dimethyl-piperidin-1-yl, 4-methyl-piperazin-1-yl, 2,6-dimethyl-morpholin-4-yl, cis-2,6-dimethyl-morpholin-4-yl, 3,5-dimethyl-morpholin-4-yl, cis-3,5-dimethyl-morpholin-4-yl, 1-oxo-thiomorpholin-4-yl or 1,1-dioxo-thiomorpholin-4-yl, for example. In another embodiment of the invention, Het is morpholin-4-yl which can be substituted by alkyl in any of the mentioned ways. In this latter embodiment, Het preferably is morpholin-4-yl which can be substituted by two $(C_1-C_4)$-alkyl substituents, i.e. Het is chosen from morpholin-4-yl and di-(($(C_1-C_4)$-alkyl)-morpholin-4-yl, and more preferably is morpholin-4-yl which can be substituted by two methyl substituents, i.e. Het is chosen from morpholin-4-yl and dimethyl-morpholin-4-yl, and particularly preferably is chosen from morpholin-4-yl, 2,6-dimethylmorpholin-4-yl and 3,5-dimethyl-morpholin-4-yl, and more particularly preferably from morpholin-4-yl and 2,6-dimethyl-morpholin-4-yl, wherein 2,6-dimethylmorpholin-4-yl and 3,5-dimethyl-morpholin-4-yl can be present in any stereoisomeric form or a mixture of stereoisomeric forms in any ratio and preferably are present in the form of cis-2,6-dimethylmorpholin-4-yl and cis-3,5-dimethyl-morpholin-4-yl. In another embodiment of the invention, Het is cis-2,6-dimethyl-morpholin-4-yl. In another embodiment of the invention, Het is unsubstituted morpholin-4-yl. In one embodiment of the invention, a fused benzene ring in the group Het is unsubstituted.

In preferred compounds according to the present invention, or preferred embodiments of the present invention, any one or more structural elements such as groups and substituents in the compounds of the formula I are defined as in any of the preferred definitions of the elements or in any specified embodiment and/or can have one or more of the specific meanings which are mentioned as examples of the elements, wherein all combinations of one or more preferred definitions and/or embodiments and/or specific meanings are a subject of the present invention. Also with respect to all preferred compounds of the formula I, all their stereoisomeric forms and mixtures of stereoisomeric forms in all ratios, and their physiologically acceptable salts are a subject of the present invention. For example, in one embodiment of the invention the employed compound is a compound of the formula I, wherein
A is 1,4-phenylene which can be substituted by one or two identical or different substituents chosen from halogen and $(C_1-C_4)$-alkyl;
$R^1$ is Het;
Het is a residue of a monocyclic 5-membered, 6-membered or 7-membered heterocycle which is saturated and contains a ring nitrogen atom via which the group Het is bonded to the group -A-S(O)$_2$—, and which can contain one further ring heteroatom chosen from nitrogen, oxygen and sulfur wherein the sulfur atom can carry one or two oxo groups, and which can be substituted by one or more identical or different $(C_1-C_4)$-alkyl substituents;
in any of its stereoisomeric forms, or a mixture of stereoisomeric forms in any ratio, or a physiologically acceptable salt thereof.

In another embodiment of the invention the employed compound is a compound of the formula I, wherein
$R^2$ is phenyl or heteroaryl which can both be substituted by one, two or three identical or different substituents chosen from halogen, $(C_1-C_4)$-alkyl and trifluoromethyl;
two of the groups $R^3$, $R^4$, $R^5$ and $R^6$ are hydrogen and the others of the groups $R^3$, $R^4$, $R^5$ and $R^6$, which are independent of each other and can be identical or different, are chosen from hydrogen, halogen, $(C_1-C_4)$-alkyl and $(C_1-C_4)$-alkyl-O—;
heteroaryl is a residue of a monocyclic 5-membered aromatic heterocycle which comprises one ring heteroatom chosen from nitrogen, oxygen and sulfur or two ring heteroatoms one of which is a nitrogen atom and the other of which is chosen from nitrogen, oxygen and sulfur;
in any of its stereoisomeric forms, or a mixture of stereoisomeric forms in any ratio, or a physiologically acceptable salt thereof.

In another embodiment of the invention the employed compound is a compound of the formula I, wherein
A is 1,4-phenylene which can be substituted by one or two identical or different substituents chosen from halogen and $(C_1-C_4)$-alkyl;
$R^1$ is Het;
$R^2$ is phenyl or heteroaryl which can both be substituted by one, two or three identical or different substituents chosen from halogen, $(C_1-C_4)$-alkyl and trifluoromethyl;
two of the groups $R^3$, $R^4$, $R^5$ and $R^6$ are hydrogen and the others of the groups $R^3$, $R^4$, $R^5$ and $R^6$, which are independent of each other and can be identical or different, are chosen from hydrogen, halogen, $(C_1-C_4)$-alkyl and $(C_1-C_4)$-alkyl-O—;
heteroaryl is a residue of a monocyclic 5-membered aromatic heterocycle which comprises one ring heteroatom chosen from nitrogen, oxygen and sulfur or two ring heteroatoms one of which is a nitrogen atom and the other of which is chosen from nitrogen, oxygen and sulfur;
Het is a residue of a monocyclic 5-membered, 6-membered or 7-membered heterocycle which is saturated and contains a ring nitrogen atom via which the group Het is bonded to the group -A-S(O)$_2$—, and which can contain one further ring heteroatom chosen from nitrogen, oxygen and sulfur wherein the sulfur atom can carry one or two oxo groups, and which can be substituted by one or more identical or different $(C_1-C_4)$-alkyl substituents;
in any of its stereoisomeric forms, or a mixture of stereoisomeric forms in any ratio, or a physiologically acceptable salt thereof.

In another embodiment of the invention the employed compound is a compound of the formula I, wherein
A is unsubstituted 1,4-phenylene;
$R^1$ is Het;
$R^2$ is phenyl or heteroaryl which can both be substituted by one, two or three identical or different substituents chosen from halogen and $(C_1-C_4)$-alkyl;
$R^3$ and $R^6$ are hydrogen, $R^4$ is chosen from hydrogen, halogen and $(C_1-C_4)$-alkyl-O—, and $R^5$ is chosen from halogen and $(C_1-C_4)$-alkyl-O—;
heteroaryl is chosen from thiophenyl and a residue of a 5-membered aromatic heterocycle which comprises a ring nitrogen atom and one further ring heteroatom chosen from nitrogen, oxygen and sulfur;
Het is a residue of a monocyclic 6-membered saturated heterocycle which contains a ring nitrogen atom via which the group Het is bonded to the group -A-S(O)$_2$—, and which can contain one further ring heteroatom chosen from oxygen and sulfur wherein the sulfur atom can carry one or two oxo groups, and which can be substituted by one, two, three or four identical or different $(C_1-C_4)$-alkyl substituents;
in any of its stereoisomeric forms, or a mixture of stereoisomeric forms in any ratio, or a physiologically acceptable salt thereof, wherein in this embodiment heteroaryl is preferably chosen from thiophenyl and isoxazolyl.

In another embodiment of the invention the employed compound is a compound of the formula I, wherein
A is unsubstituted 1,4-phenylene;
$R^1$ is Het;
$R^2$ is heteroaryl which can be substituted by one, two or three identical or different substituents chosen from halogen and $(C_1-C_4)$-alkyl;

$R^3$, $R^4$ and $R^6$ are hydrogen and $R^5$ is chlorine;
heteroaryl is chosen from thiophenyl and isoxazolyl;
Het is morpholin-4-yl which can be substituted by two methyl substituents;
in any of its stereoisomeric forms, or a mixture of stereoisomeric forms in any ratio, or a physiologically acceptable salt thereof.

In another embodiment of the invention the employed compound of the formula I is chosen from
2-(4-chloro-phenylsulfonylamino)-4,5-dimethoxy-N-(4-(thiomorpholine-4-sulfonyl)-phenyl)-benzamide,
2-(4-chloro-phenylsulfonylamino)-N-(4-(cis-2,6-dimethyl-morpholine-4-sulfonyl)-phenyl)-4,5-dimethoxy-benzamide,
5-chloro-2-(5-chloro-thiophene-2-sulfonylamino)-N-(4-(morpholine-4-sulfonyl)-phenyl)-benzamide, and
5-chloro-2-(3,5-dimethyl-isoxazole-4-sulfonylamino)-N-(4-(cis-2,6-dimethyl-morpholine-4-sulfonyl)-phenyl)-benzamide,
or a physiologically acceptable salt thereof,
and preferably is chosen from 5-chloro-2-(5-chloro-thiophene-2-sulfonylamino)-N-(4-(morpholine-4-sulfonyl)-phenyl)-benzamide and 5-chloro-2-(3,5-dimethyl-isoxazole-4-sulfonylamino)-N-(4-(cis-2,6-dimethyl-morpholine-4-sulfonyl)-phenyl)-benzamide, or a physiologically acceptable salt thereof. In another embodiment of the invention the employed compound of the formula I is 5-chloro-2-(5-chloro-thiophene-2-sulfonylamino)-N-(4-(morpholine-4-sulfonyl)-phenyl)-benzamide or a physiologically acceptable salt thereof.

In another embodiment of the invention a compound of the formula I, in any of its stereoisomeric forms or a mixture of stereoisomeric forms in any ratio, or a physiologically acceptable salt thereof is employed wherein the physiologically acceptable salt is a sodium salt. In another embodiment of the invention a compound is employed which is chosen from
2-(4-chloro-phenylsulfonylamino)-4,5-dimethoxy-N-(4-(cis-2,6-dimethyl-morpholine-4-sulfonyl)-phenyl)-benzamide sodium salt,
5-chloro-2-(5-chloro-thiophene-2-sulfonylamino)-N-(4-(morpholine-4-sulfonyl)-phenyl)-benzamide sodium salt, and
5-chloro-2-(3,5-dimethyl-isoxazole-4-sulfonylamino)-N-(4-(cis-2,6-dimethyl-morpholine-4-sulfonyl)-phenyl)-benzamide sodium salt,
and preferably is chosen from 5-chloro-2-(5-chloro-thiophene-2-sulfonylamino)-N-(4-(morpholine-4-sulfonyl)-phenyl)-benzamide sodium salt and 5-chloro-2-(3,5-dimethyl-isoxazole-4-sulfonylamino)-N-(4-(cis-2,6-dimethyl-morpholine-4-sulfonyl)-phenyl)-benzamide sodium salt. In another embodiment of the invention the employed compound is 5-chloro-2-(5-chloro-thiophene-2-sulfonylamino)-N-(4-(morpholine-4-sulfonyl)-phenyl)-benzamide sodium salt.

The compounds of the formula I can be prepared as described in WO 00/02851 and U.S. Pat. No. 6,335,334, the contents of which with respect to the preparation of the compounds are incorporated herein by reference, and as exemplarily outlined in the following. In one process, first an anthranilic acid of the formula II is reacted with a sulfonyl chloride of the formula $R^2$—$S(O)_2$—Cl or a sulfonic acid anhydride in the presence of a base in a solvent like water, pyridine or an ether, for example, to give a compound of the formula III. Suitable bases are inorganic bases like sodium carbonate or organic bases like, for example, pyridine or triethylamine. In the starting compounds and intermediates of the formulae II and III, as well as in the compounds of the formulae IV, V and VI and the other starting compounds and intermediates in the synthesis, the groups A and $R^1$ to $R^6$ are defined as in the compounds of the formula I. The sulfonylaminobenzoic acid of the formula III can then be activated, for example by reaction with a chlorinating agent like phosphorus pentachloride, phosphorus oxychloride or thionyl chloride in an inert solvent, to give an acid chloride of the formula IV which subsequently is reacted with an optionally substituted aniline.

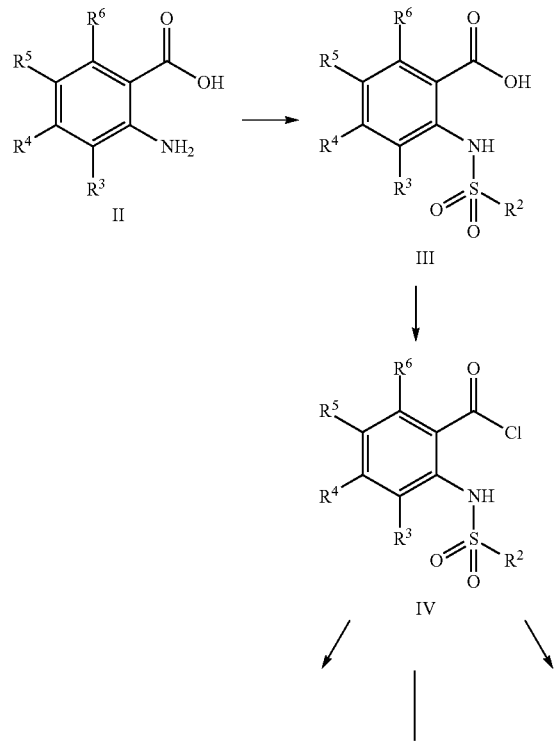

-continued

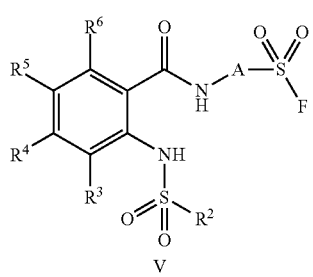

V

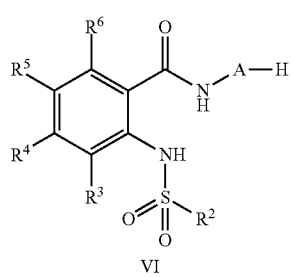

VI

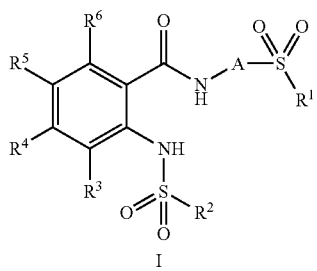

I

The activation of the carboxylic acid group in the compounds of the formula III can also be carried our in a different manner, for example by one of the numerous methods for the formation of amide bonds in peptide chemistry which are well known to the skilled person, for example by conversion into a mixed anhydride or an activated ester or by using a carbodiimide like dicyclohexylcarbodiimide. The reaction of the activated sulfonylaminobenzoic acid with an optionally substituted aniline is favorably carried out in an inert solvent such as, for example, pyridine, tetrahydrofuran or toluene in the absence or in the presence of an inert auxiliary base like, for example, a tertiary amine or pyridine. The optionally substituted aniline which is employed in the reaction with the activated acid, can already contain the group $R^1$—$S(O)_2$— and be a compound of the formula $R^1$—$S(O)_2$-A-$NH_2$, and the reaction then directly provides the final compound of the formula I. The activated acid can also first be reacted with an optionally substituted aniline of the formula H-A-$NH_2$. The resulting reaction product of the formula VI can then be chlorosulfonated under standard conditions and the introduced chlorosulfonyl group subsequently converted under standard conditions into the group $R^1$—$S(O)_2$—, for example by reaction with an amine of the formula $R^7R^8N$—H or Het-H in substance or in a solvent like N-methylpyrrolidone, dimethylformamide, toluene or an ether, optionally in the presence of an auxiliary base. In a similar manner the activated acid can be reacted with an optionally substituted fluorosulfonylaniline of the formula F—$S(O)_2$-A-$NH_2$ and the obtained fluorosulfonyl intermediate of the formula V converted under standard conditions into the compound of the formula I by reaction with an amine of the formula $R^7R^8N$—H or Het-H.

Compounds of the formula I can also be obtained by first activating a nitrobenzoic acid of the formula VII, for example by converting it into the respective acid chloride of the formula VIII or by another procedure as mentioned above, and then reacting it with an aniline of the formula $R^1$—$S(O)_2$-A-$NH_2$ analogously to the procedures described above to give a compound of the formula X. In the starting compounds and intermediates of the formulae VII, VIII and X, as well as in the compounds of the formula IX and XI and the other starting compounds and intermediates in the synthesis, the groups A and $R^1$ to $R^6$ are defined as in the compounds of the formula I. In this process, too, as the aniline an optionally substituted fluorosulfonylaniline of the formula F—$S(O)_2$-A-$NH_2$ can be employed and in the obtained fluorosulfonyl intermediate of the formula IX the fluorosulfonyl group converted under standard conditions into the group $R^1$—$S(O)_2$— by reaction with an amine of the formula $R^7R^8N$—H or Het-H.

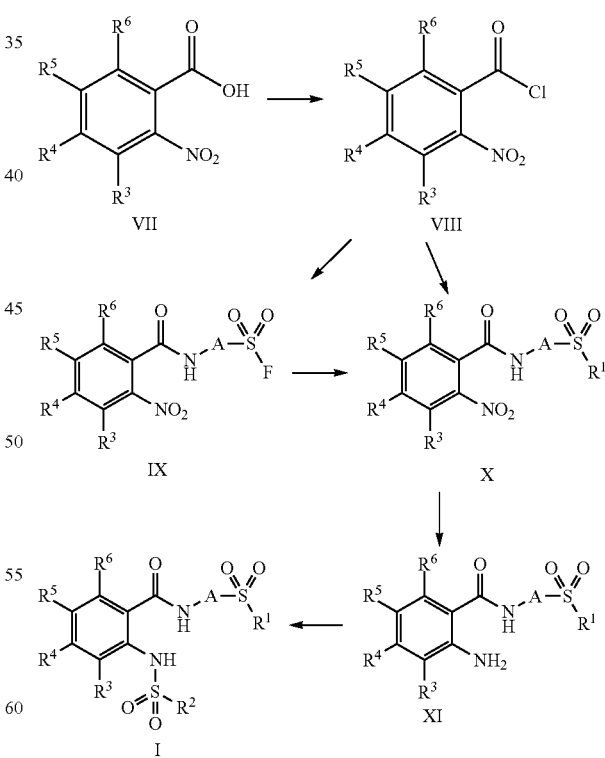

The reduction of the nitro group in the obtained nitro intermediates of the formula X to give an amino group can be carried out, for example, by catalytic hydrogenation in the presence of a noble metal catalyst or Raney nickel in a solvent like ethanol, glacial acetic acid or a ethanolic solution of hydrogen chloride, or it can be carried out by reduction with a metal like zinc, tin or iron in the presence of an acid. The reduction can also be carried out, for example, with tin(II) chloride or by reaction with sodium dithionite, favorably in a mixture of methanol, tetrahydrofuran and water as solvent. The sulfonylation of the amino group in the reduction product of the formula XI with an activated sulfonic acid derivative can be carried out analogously to the reactions described above, for example with a sulfonic acid chloride of the formula $R^2—S(O)_2—Cl$ in pyridine, and finally gives the compound of the formula I.

All reactions for the synthesis of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. Depending on the circumstances of the individual case, in order to avoid side reactions during the synthesis of a compound of the formula I, it can be necessary or advantageous to temporarily block functional groups by introducing protective groups and deprotect them in a later stage of the synthesis, or introduce functional groups in the form of precursor groups which in a later reaction step are converted into the desired functional groups. Such synthetic strategies and protective groups and precursor groups which are suitable in an individual case, are known to the skilled person. If desired, the compounds of the formula I can be purified by customary purification procedures, for example by recrystallization or chromatography. The starting compounds for the preparation of the compounds of the formula I are commercially available or can be prepared according to, or analogously to, literature procedures.

As is described in WO 00/02851 and U.S. Pat. No. 6,335, 334 and can be demonstrated in tests known to the person skilled in the art, for example the tests described in U. Schindler et al., Mol. Pharmacol. 69 (2006), 1260-1268, and in the tests described in WO 00/02851 and U.S. Pat. No. 6,335,334, the contents of which with respect to the pharmacological characterization of the compounds are incorporated herein by reference, the compounds of the formula I activate the hemeprotein enzyme soluble guanylate cyclase (soluble guanylyl cyclase, sGC). They do not act via release of NO (nitric oxide) and activate also sGC which is NO-insensitive and in which the heme-iron is present in the ferric redox form. A subject of the present invention also is the use of an activator or stimulator of soluble guanylate cyclase (sGC), in particular the use of an activator or stimulator of sGC which does not act via release of NO, including the use of an activator of NO-insensitive sGC and the use of an activator of sGC in which the heme-iron is present in the ferric redox form, for manufacturing a medicament for the treatment of pain, as well as any such sGC activator or stimulator for use in the treatment of pain, a method of treating pain which comprises administering to a subject in need thereof any such sGC activator or stimulator, and a pharmaceutical composition for use in the treatment of pain which comprises any such sGC activator or stimulator and a pharmaceutically acceptable carrier. Besides the compounds of the formula I, as examples of compounds which activate or stimulate sGC, (5-(1-benzyl-1H-indazol-3-yl)-furan-2-yl)-methanol, 5-cyclopropyl-2-(1-(2-fluoro-benzyl)-1H-pyrazolo[3,4-b]pyridin-3-yl)-pyrimidin-4-ylamine, 2-(1-(2-fluoro-benzyl)-1H-pyrazolo[3,4-b]pyridin-3-yl)-5-(morpholin-4-yl)-pyrimidine-4,6-diamine, 3-(3-dimethylamino-propoxy)-N-(4-methoxy-phenyl)-1-benzyl-1H-pyrazole-5-carboxamide, 3-(2-(4-chloro-phenylsulfany)-phenyl)-N-(4-dimethylamino-butyl)-acrylamide and 4-(((4-carboxy-butyl)-(2-(2-(4-(2-phenyl-ethyl)-benzyloxy)-phenyl)-ethyl)-amino)-methyl)-benzoic acid may be mentioned (cf. O. V. Evgenov et al., Nature Reviews Drug Discovery 5 (2006), 755-768). All statements made above and below with respect to the use of the compounds of the formula I in the treatment of pain apply likewise to the use of an activator or stimulator of sGC in the treatment of pain.

The suitability of the compounds of the formula I for treating pain can be demonstrated in various models which are known to a person skilled in the art, for example in the models in mice described below. Due to their pronounced analgetic activity which has surprisingly been found, the compounds of the formula I and their physiologically acceptable salts can be used in animals, in particular in mammals including humans, as medicaments on their own, in mixtures with one another, for example as a mixture of two compounds of the formula I and/or their physiologically acceptable salts, or together with other pharmacologically active compounds, in the treatment of pain. Preferably the compounds of the formula I and their physiologically acceptable salts are used for this purpose in the form of pharmaceutical compositions which comprise at least one compound of the formula I or a physiologically acceptable salt thereof and a pharmaceutically acceptable carrier, i.e. one or more pharmaceutically acceptable carrier substances, or vehicles, and/or additives, or auxiliary substances.

The treatment of pain by means of the compounds of the formula I and/or their physiologically acceptable salts includes the treatment of acute pain as well as the treatment of chronic pain. Treatment of pain, as understood herein, comprises both the therapy of existing pain with the aim of alleviation or relief or painlessness, and the prophylaxis or prevention of pain in humans or animals which are susceptible to the occurrence of pain because of any existing disease or a painful medical procedure, for example, and are in need of such a prophylaxis or prevention, with the aim of a prevention or suppression of the occurrence of pain or an attenuation in the case of its occurrence. Examples of chronic pain are pain associated with a chronic musculoskeletal disease including back pain, pain associated with menstrual bleeding, pain associated with a joint disease including pain associated with osteoarthritis and pain associated with rheumatoid arthritis, inflammatory pain including pain associated with intestinal inflammation and pain associated with cardiac muscle inflammation, pain associated with multiple sclerosis, pain associated with neuritis, pain associated with a carcinoma, pain associated with a sarcoma, pain associated with AIDS, pain associated with chemotherapy, amputation pain, trigeminus neuralgia, headache including migraine cephalalgia, and neuropathic pain including post-herpes zoster neuralgia, neuropathic pain caused by metabolic dysfunctions such as diabetes mellitus, neuropathic pain associated with diabetic polyneuropathy, neuropathic pain following a surgical intervention and chemotherapy-induced neuropathic pain. Examples of acute pain are pain following an injury, post-operative pain, pain associated with an attack of gout, toothache, pain associated with a jaw-bone surgery intervention and acute herpes zoster pain. In one embodiment of the invention, a compound of the formula I or a physiologically acceptable salt thereof is used for the treatment of acute pain including any of the aforementioned examples thereof. In another embodiment of the invention, a compound of the formula I or a physiologically acceptable salt thereof is used for the treatment of chronic pain including any of the aforementioned examples thereof, for example the treatment of pain associated with a joint disease, inflammatory pain or neuropathic pain, or the treatment of inflammatory pain or neuropathic pain, including any of the aforementioned examples thereof. In another embodiment of the invention, a compound of the formula I or a physiologically acceptable salt thereof is used for the treatment of pain associated with a joint disease including any of the aforementioned examples thereof, such as the treatment of pain associated with osteoarthritis or pain associated with rheumatoid arthritis. In another embodiment of the invention, a compound of the formula I or a physiologically acceptable salt thereof is used for the treatment of inflammatory pain including any of the aforementioned examples thereof, such as the treatment of pain associated with intestinal inflammation or pain associated with cardiac muscle inflammation. In another embodiment of the invention, a compound of the formula I or a physiologically acceptable salt thereof is used for the treatment of neuropathic pain including any of the aforementioned examples thereof, such as the treatment of post-herpes zoster neuralgia, neuropathic pain caused by metabolic dysfunctions such as diabetes mellitus, neuropathic pain associated with diabetic polyneuropathy, neuropathic pain following a surgical intervention or chemotherapy-induced neuropathic pain.

Medicaments and pharmaceutical compositions which are to be used according to the invention and which comprise a compound of the formula I and/or a physiologically acceptable salt thereof, can be administered enterally, for example orally or rectally, for example in the form of pills, tablets, film tablets, sugar-coated tablets, granules, hard gelatin capsules, soft gelatin capsules, microcapsules, suppositories, solutions, such as aqueous, alcoholic or oily solutions, juices, drops, syrups, suspensions or emulsions. The medicaments and pharmaceutical compositions can also be administered parenterally, for example subcutaneously, intramuscularly, intravenously, intraperitoneally, intrathecally or intraarticularly, in the form of injection solutions or infusion solutions, for example. Other examples of suitable forms of administration are percutaneous, transdermal and topical administration, for example in the form of ointments, creams, pastes, lotions, gels, sprays, powders, foams, aerosols or solutions, administration in the form of implants and inhalative administration. The pharmaceutical compositions can also exhibit a protracted release of the active compound.

The pharmaceutical compositions which are to be used according to the invention can be produced using standard methods for producing pharmaceutical compositions which are known to a person skilled in the art. For this, one or more compounds of the formula I and/or their physiologically acceptable salts are mixed with one or more solid or liquid galenical carrier substances and/or additives and, if a combination product is to be produced, one or more other pharmacologically active ingredients, and brought into a suitable form for administration and dosage which can then be used as a medicament in human medicine or veterinary medicine. The pharmaceutical compositions comprise an effective dose of the compound of the formula I and/or a physiologically acceptable salt thereof which normally amounts to from about 0.5 to about 90 percent by weight of the pharmaceutical composition. The quantity of active compound of the formula I and/or its physiologically acceptable salt in the dosage unit of the pharmaceutical compositions normally is from about 0.2 mg to about 1000 mg, preferably from about 1 mg to about 500 mg, but it can also be higher depending on the nature of the pharmaceutical composition. A further subject of the invention is a process for manufacturing a medicament or a pharmaceutical composition for the treatment of pain which comprises bringing a compound of the formula I or a physiologically acceptable salt thereof and one or more pharmaceutically acceptable carrier substances and additives, and optionally one or more other pharmacologically active compounds, into a form for administration and dosage.

As carrier substances for producing a pharmaceutical composition, organic or inorganic substances can be used which are suitable for the intended use, for example for oral or parenteral administration, and do not react with the active compounds in an undesirable manner, for example water, saline, vegetable oils, alcohols, such as ethanol, isopropanol, benzyl alcohols, 1,2-propanediol, glycerol, polyethylene glycols, glyceryl triacetate, gelatin, carbohydrates and derivatives such as lactose, mannitol or starch, talc, lanolin, vaseline or magnesium carbonate. It is also possible to use mixtures of two or more carrier substances, for example mixtures of two or more solvents, such as mixtures of one or more organic solvents with water. Additives, or auxiliary substances, which can be present in the pharmaceutical compositions, include stabilizing agents, wetting agents, dispersants, emulsifiers, solubilizers, thickeners, salts, for example for influencing the osmotic pressure, glidants, preservatives, dyes, flavorings, aromatizing substances and buffering substances, such as stearic acid, magnesium stearate, polyvinylpyrrolidone, sodium chloride, silica and cellulose derivatives, for example. The pharmaceutical compositions can also comprise one or more other active ingredients. The compounds of the formula I and their physiologically acceptable salts can also be lyophilized and the resulting lyophilisates used for producing injection compositions and infusion compositions, for example. From the compounds of the formula I and their physiologically acceptable salts, also liposomal preparations can be prepared and used for topical administration, for example.

The dosage of the compounds of the formula and/or their physiologically acceptable salts in the use according to the invention depends on the specific case and, as usual, has to be adapted individually by the physician in order to achieve an optimal effect. For example, it depends on the sex, age, weight and individual responsiveness of the human or animal to be treated, on the strength and duration of action of the compound employed, on whether an acute or a chronic case is treated, on whether therapy or prophylaxis is performed, on whether the treatment is performed over a relatively long period of time, or on whether other active compounds are administered in addition to compounds of the formula I. In general, a dose range for treating pain in humans of from about 0.1 mg/kg to about 100 mg/kg, preferably from about 1 mg/kg to about 30 mg/kg, more preferably from about 1 mg/kg to about 10 mg/kg, i.e. mg per kg of body weight per day, is appropriate for achieving the intended effect in case of administration to an adult weighing about 75 kg. The daily dose can be administered as a single dose or subdivided into several individual doses, for example one, two, three or four individual doses. The compounds of the formula and/or their physiologically acceptable salts can also be administered as a bolus or continuously, for example by means of infusion or continuous infusion. Depending of the specific case, it may be necessary to deviate upwards or downwards from the mentioned doses.

EXAMPLE COMPOUNDS AND INTERMEDIATES 1) 2-(4-Chloro-phenylsulfonylamino)-4,5-dimethoxy-benzoic acid 33.71 g (0.32 mol) of sodium carbonate were dissolved in 250 ml of water and warmed to 60° C. 25.00 g (0.13 mol) of 2-amino-4,5-dimethoxy-benzoic acid were introduced into the solution, and to this solution 29.55 g (0.14 mol) of 4-chloro-benzenesulfonyl chloride were added portionwise over 15 min. After cooling, the mixture was filtered with suction, the residue was taken up in 1% sodium hydrogencarbonate solution, the solution filtered, and the product precipitated by addition of 1 N hydrochloric acid. 25.90 g (55%) of 2-(4-chloro-phenylsulfonylamino)-4,5-dimethoxy-benzoic acid of melting point (M.p.) 212-214° C. were obtained.

Analogously were obtained:

2) 5-Chloro-2-(4-chloro-phenylsulfonylamino)-benzoic acid; M.p.: 210° C.

3) 5-Chloro-2-(3,4-dichloro-phenylsulfonylamino)-benzoic acid 4) 2-(4-Chloro-phenylsulfonylamino)-5-methyl-benzoic acid; M.p.: 201° C.

5) 2-(4-Chloro-phenylsulfonylamino)-4,5-dimethoxy-benzoyl chloride 25.90 g (0.07 mol) of 2-(4-chloro-phenylsulfonylamino)-4,5-dimethoxy-benzoic acid were mixed with 75 ml of toluene, 17.30 g (0.08 mol) of phosphorus pentachloride were added and the mixture was stirred at 40-45° C. for 2.5 h. Then the mixture was concentrated in vacuo to half of its volume and the product that precipitated was filtered off with suction and washed with a small amount of toluene. 25.30 g (93%) of 2-(4-chloro-phenylsulfonylamino)-4,5-dimethoxy-benzoyl chloride having a melting point of 175-177° C. were obtained.

Analogously were obtained:

6) 5-Chloro-2-(4-chloro-phenylsulfonylamino)-benzoyl chloride; M.p.: 127° C.

7) 5-Chloro-2-(3,4-dichloro-phenylsulfonylamino)-benzoyl chloride; M.p.: 117° C.

8) 2-(4-Chloro-phenylsulfonylamino)-5-methyl-benzoyl chloride; M.p.: 114° C.

9) 4-((2-(4-Chloro-phenylsulfonylamino)-4,5-dimethoxy-benzoyl)-amino)-benzenesulfonyl fluoride 10.00 g (25.6 mmol) of 2-(4-chloro-phenylsulfonylamino)-4,5-dimethoxy-benzoyl chloride were mixed with 300 ml of toluene, 4.49 g (25.6 mmol) of 4-aminobenzenesulfonyl fluoride were added and the mixture was heated under reflux for 4 h. After cooling, the precipitated solid was filtered off with suction and washed with toluene. 11.71 g (87%) of the title compound having a melting point of 216-219° C. were obtained.

Analogously were obtained:

10) 4-((5-Chloro-2-(4-chloro-phenylsulfonylamino)-benzoyl)-amino)-benzenesulfonyl fluoride; M.p.: 242° C.

11) 4-((5-Chloro-2-(3,4-dichloro-phenylsulfonylamino)-benzoyl)-amino)-benzenesulfonyl fluoride; M.p.: 232° C.

12) 4-((2-(4-Chloro-phenylsulfonylamino)-5-methyl-benzoyl)-amino)-benzenesulfonyl fluoride; M.p.: 224° C.

13) 3-((5-Chloro-2-(4-chloro-phenylsulfonylamino)-benzoyl)-amino)-benzenesulfonyl fluoride; M.p.: 224° C.

14) 2-(4-Chloro-phenylsulfonylamino)-4,5-dimethoxy-N-(4-(thiomorpholine-4-sulfonyl)-phenyl)-benzamide 500 mg (0.95 mmol) of 4-((2-(4-chloro-phenylsulfonylamino)-4,5-dimethoxy-benzoyl)-amino)-benzenesulfonyl fluoride were dissolved in 1 ml of thiomorpholine and heated to 90° C. for 30 min. For working up, the mixture was poured onto 50 ml of ice/1 N hydrochloric acid, the precipitate was filtered off with suction, dried in a vacuum-drying chamber over phosphorus pentoxide and recrystallized from hexane/ethyl acetate. 378 mg (65%) of the title compound having a melting point of 241° C. were obtained.

Analogously were obtained:

15) 5-Chloro-2-(4-chloro-phenylsulfonylamino)-N-(4-(thiomorpholine-4-sulfonyl)-phenyl)-benzamide; M.p.: 246° C.

16) 5-Chloro-2-(4-chloro-phenylsulfonylamino)-N-(4-(4-methyl-piperazine-1-sulfonyl)-phenyl)-benzamide; M.p.: 219° C.

17) 5-Chloro-2-(4-chloro-phenylsulfonylamino)-N-(4-(2,6-dimethyl-morpholine-4-sulfonyl)-phenyl)-benzamide; M.p.: 259° C.

18) 5-Chloro-2-(4-chloro-phenylsulfonylamino)-N-(4-(cis-2,6-dimethyl-morpholine-4-sulfonyl)-phenyl)-benzamide; M.p.: 251° C.

19) 5-Chloro-2-(3,4-dichloro-phenylsulfonylamino)-N-(4-(morpholine-4-sulfonyl)-phenyl)-benzamide; M.p.: 253° C.

20) 5-Chloro-2-(3,4-dichloro-phenylsulfonylamino)-N-(4-(thiomorpholine-4-sulfonyl)-phenyl)-benzamide; M.p.: 222° C.

21) 5-Chloro-2-(3,4-dichloro-phenylsulfonylamino)-N-(4-(4-methyl-piperazine-1-sulfonyl)-phenyl)-benzamide; M.p.: 246° C.

22) 2-(4-Chloro-phenylsulfonylamino)-4,5-dimethoxy-N-(4-(morpholine-4-sulfonyl)-phenyl)-benzamide; M.p.: 172° C.

23) 5-Chloro-2-(4-chloro-phenylsulfonylamino)-N-(4-diethylsulfamoyl-phenyl)-benzamide; M.p.: 226° C.

24) 5-Chloro-2-(4-chloro-phenylsulfonylamino)-N-(4-(piperidine-1-sulfonyl)-phenyl)-benzamide; M.p.: 240° C.

25) 5-Chloro-2-(4-chloro-phenylsulfonylamino)-N-(4-(2-methoxy-ethylsulfamoyl)-phenyl)-benzamide; M.p.: 209° C.

26) 2-(4-Chloro-phenylsulfonylamino)-5-methyl-N-(4-(morpholine-4-sulfonyl)-phenyl)-benzamide; M.p.: 203° C.

27) 5-Chloro-2-(4-chloro-phenylsulfonylamino)-N-(3-(morpholine-4-sulfonyl)-phenyl)-benzamide; M.p.: 238° C.

28) 5-Chloro-2-(4-chloro-phenylsulfonylamino)-N-(3-(thiomorpholine-4-sulfonyl)-phenyl)-benzamide; M.p.: 202° C.

29) 5-Chloro-2-(4-chloro-phenylsulfonylamino)-N-(3-(4-methyl-piperazine-1-sulfonyl)-phenyl)-benzamide hydrochloride; M.p.: 245° C.

30) 5-Chloro-2-(4-chloro-phenylsulfonylamino)-N-(4-(morpholine-4-sulfonyl)-phenyl)-benzamide; M.p.: 228° C.

31) 2-(4-Chloro-phenylsulfonylamino)-5-methyl-N-(4-(thiomorpholine-4-sulfonyl)-phenyl)-benzamide hydrochloride; M.p.: 234° C.

32) 2-(4-Chloro-phenylsulfonylamino)-4,5-dimethoxy-N-(4-(4-methyl-piperazine-1-sulfonyl)-phenyl)-benzamide; M.p.: 172° C.

33) 2-(4-Chloro-phenylsulfonylamino)-N-(4-(cis-2,6-dimethyl-morpholine-4-sulfonyl)-phenyl)-4,5-dimethoxy-benzamide; M.p.: 208° C.

34) 2-(4-Chloro-phenylsulfonylamino)-4,5-dimethoxy-N-(4-(thiazolidine-3-sulfonyl)-phenyl)-benzamide; M.p.: 261° C.

35) 2-(4-Chloro-phenylsulfonylamino)-N-(4-(2,5-dihydro-1H-pyrrole-1-sulfonyl)-phenyl)-4,5-dimethoxy-benzamide; M.p.: 262° C.

36) 2-(4-Chloro-phenylsulfonylamino)-N-(4-(1,2,3,6-tetrahydro-pyridine-1-sulfonyl)-phenyl)-4,5-dimethoxy-benzamide; M.p.: 252° C.

37) 2-(4-Chloro-phenylsulfonylamino)-4,5-dimethoxy-N-(4-(2-methyl-piperidine-1-sulfonyl)-phenyl)-benzamide; M.p.: 227° C.

38) 2-(4-Chloro-phenylsulfonylamino)-4,5-dimethoxy-N-(4-(piperazine-1-sulfonyl)-phenyl)-benzamide; M.p.: 243° C.
39) 2-(4-Chloro-phenylsulfonylamino)-4,5-dimethoxy-N-(4-(4-methyl-piperidine-1-sulfonyl)-phenyl)-benzamide; M.p.: 267° C.
40) 2-(4-Chloro-phenylsulfonylamino)-4,5-dimethoxy-N-(4-(4-methyl-perhydro-[1,4]diazepine-1-sulfonyl)-phenyl)-benzamide; M.p.: 274° C.
41) 2-(4-Chloro-phenylsulfonylamino)-N-(4-(4-ethyl-piperazine-1-sulfonyl)-phenyl)-4,5-dimethoxy-benzamide; M.p.: 191° C.
42) 2-(4-Chloro-phenylsulfonylamino)-N-(4-((2-dimethylamino-ethyl)-ethyl-sulfamoyl)-phenyl)-4,5-dimethoxy-benzamide; M.p.: Dec. >119° C.
43) 2-(4-Chloro-phenylsulfonylamino)-N-(4-(1,4,5,6-tetrahydro-pyrimidine-1-sulfonyl)-phenyl)-4,5-dimethoxy-benzamide; M.p.: Dec. >237° C.
44) 2-(4-Chloro-phenylsulfonylamino)-N-(4-(indan-1-ylsulfamoyl)-phenyl)-4,5-dimethoxy-benzamide; M.p.: 161° C.
45) 2-(4-Chloro-phenylsulfonylamino)-N-(4-cyclopropylsulfamoyl-phenyl)-4,5-dimethoxy-benzamide; M.p.: 222° C.
46) N-(4-(Allyl-cyclohexyl-sulfamoyl)-phenyl)-2-(4-chloro-phenylsulfonylamino)-4,5-dimethoxy-benzamide; M.p.: 182° C.
47) 5-Chloro-2-nitro-benzoyl chloride 100.00 g (0.50 mol) of 5-chloro-2-nitrobenzoic acid were mixed with 72.20 g (0.61 mol) of thionyl chloride, and the mixture was heated under reflux for 2 h. The excess thionyl chloride was removed in vacuo. 106.50 g (ca. 98%) of crude 5-chloro-2-nitro-benzoyl chloride were obtained as an oil.

Analogously was obtained:
48) 5-Methyl-2-nitro-benzoyl chloride; Oil
49) 4-(5-Chloro-2-nitro-benzoylamino)-benzenesulfonyl fluoride 86.00 g (0.39 mol) of 5-chloro-2-nitro-benzoyl chloride was dissolved in 300 ml of toluene, a solution of 62.00 g (0.35 mol) of 4-aminobenzenesulfonyl fluoride was added dropwise, and the mixture was heated under reflux for 4 h. Subsequently it was cooled, concentrated in vacuo to half of its volume, cooled, and the precipitated solid was filtered off with suction. 121.60 g (86%) of the title compound having a melting point of 182-184° C. were obtained.

Analogously was obtained:
50) 4-(5-Methyl-2-nitro-benzoylamino)-benzenesulfonyl fluoride; M.p.: 179° C.
51) 5-Chloro-N-(4-(morpholine-4-sulfonyl)-phenyl)-2-nitro-benzamide 120.00 g (0.33 mol) of 4-(5-chloro-2-nitro-benzoylamino)-benzenesulfonyl fluoride, 29.10 g (0.33 mol) of morpholine and 33.85 g (0.33 mol) of triethylamine were stirred in 1200 ml of toluene at 60° C. for 2 days. The precipitated solid was filtered off with suction and recrystallized from acetone/n-hexane. 102.10 g (71%) of the title compound having a melting point of 243-245° C. were obtained.

Analogously were obtained:
52.) 5-Chloro-2-nitro-N-(4-(thiomorpholine-4-sulfonyl)-phenyl)-benzamide; M.p.: 120° C.
53) 5-Methyl-N-(4-(morpholine-4-sulfonyl)-phenyl)-2-nitro-benzamide; M.p.: 249° C.
54) 2-Amino-5-chloro-N-(4-(morpholine-4-sulfonyl)-phenyl)-benzamide 11.10 g (26.1 mmol) of 5-chloro-N-(4-(morpholine-4-sulfonyl)-phenyl)-2-nitro-benzamide were dissolved in 440 ml of tetrahydrofuran/methanol (1:1) and a solution of 27.23 g (156.4 mmol) of sodium dithionite in 330 ml of water was added dropwise. After stirring for 1 h at room temperature, the organic solvents were removed in a rotary evaporator, and the precipitated product was filtered off with suction and purified by chromatography over silica with methylene chloride/methanol (9:1). 5.68 g (55%) of the title compound having a melting point of 229-231° C. were obtained.

Analogously was obtained:
55) 2-Amino-5-chloro-N-(4-(thiomorpholine-4-sulfonyl)-phenyl)-benzamide; M.p.: 177° C.
56) 5-Chloro-2-(5-chloro-1,3-dimethyl-1H-pyrazole-4-sulfonyl-amino)-N-(4-(thiomorpholine-4-sulfonyl)-phenyl)-benzamide 250 mg (0.60 mmol) of 2-amino-5-chloro-N-(4-(thiomorpholine-4-sulfonyl)-phenyl)-benzamide were dissolved in 10 ml of dry pyridine, and a solution of 195 mg (0.85 mmol) 5-chloro-1,3-dimethyl-1H-pyrazole-4-sulfonyl chloride in 5 ml of pyridine was added dropwise at 0° C. After 2 h the mixture was poured onto ice, the precipitated solid was filtered off with suction and purified by chromatography over silica with methylene chloride/methanol (98:2). 250 mg (69%) of the title compound having a melting point of 215-216° C. were obtained.

Analogously were obtained:
57) 5-Chloro-N-(4-(morpholine-4-sulfonyl)-phenyl)-2-(4-methyl-phenylsulfonylamino)-benzamide; M.p.: 214° C.
58) 5-Chloro-2-(3,4-dimethoxy-phenylsulfonylamino)-N-(4-(morpholine-4-sulfonyl)-phenyl)-benzamide; M.p.: 245° C.
59) 5-Chloro-N-(4-(morpholine-4-sulfonyl)-phenyl)-2-(4-trifluoromethoxy-phenylsulfonylamino)-benzamide; M.p.: 195° C.
60) 2-((4-Acetylamino-phenyl)-sulfonylamino)-5-chloro-N-(4-(morpholine-4-sulfonyl)-phenyl)-benzamide; M.p.: 198° C.
61) 5-Chloro-2-(5-chloro-thiophene-2-sulfonylamino)-N-(4-(morpholine-4-sulfonyl)-phenyl)-benzamide; M.p.: 112° C.
62) 5-Chloro-2-(5-chloro-1,3-dimethyl-pyrazole-4-sulfonylamino)-N-(4-(morpholine-4-sulfonyl)-phenyl)-benzamide; M.p.: 161° C.
63) 5-Chloro-2-((1-methyl-imidazole-4-sulfonyl)-amino)-N-(4-(morpholine-4-sulfonyl)-phenyl)-benzamide; M.p.: 141° C.
64) 5-Chloro-N-(4-(morpholine-4-sulfonyl)-phenyl)-2-(pyridine-3-sulfonylamino)-benzamide; M.p.: 222° C.
65) 2-((2-Acetylamino-4-methyl-thiazole-5-sulfonyl)-amino)-5-chloro-N-(4-(morpholine-4-sulfonyl)-phenyl)-benzamide; M.p.: 257° C.
66) 5-Chloro-N-(4-(morpholine-4-sulfonyl)-phenyl)-2-(thiophene-2-sulfonylamino)-benzamide; M.p.: 216° C.
67) 5-Chloro-N-(4-(morpholine-4-sulfonyl)-phenyl)-2-(4-trifluoromethyl-phenylsulfonylamino)-benzamide; M.p.: 264° C.
68) 2-(4-Bromo-phenylsulfonylamino)-5-chloro-N-(4-(morpholine-4-sulfonyl)-phenyl)-benzamide; M.p.: 232° C.
69) 2-(3,5-Bis-trifluoromethyl-phenylsulfonylamino)-5-chloro-N-(4-(morpholine-4-sulfonyl)-phenyl)-benzamide; M.p.: 209° C.
70) 5-Chloro-N-(4-(morpholine-4-sulfonyl)-phenyl)-2-(4-nitro-phenylsulfonylamino)-benzamide; M.p.: 239° C.
71) 5-Chloro-2-(4-cyano-phenylsulfonylamino)-N-(4-(morpholine-4-sulfonyl)-phenyl)-benzamide; M.p.: 238° C.
72) 5-Chloro-2-(4-methylsulfonyl-phenylsulfonylamino)-N-(4-(morpholine-4-sulfonyl)-phenyl)-benzamide; M.p.: 181° C.

73) 5-Chloro-2-(4-isopropyl-phenylsulfonylamino)-N-(4-(morpholine-4-sulfonyl)-phenyl)-benzamide; M.p.: 105° C.

74) 5-Chloro-2-(4,5-dibromo-thiophene-2-sulfonylamino)-N-(4-(morpholine-4-sulfonyl)-phenyl)-benzamide; M.p.: 232° C.

75) 5-Chloro-2-(4-fluoro-phenylsulfonylamino)-N-(4-(morpholine-4-sulfonyl)-phenyl)-benzamide; M.p.: 245° C.

76) 5-Chloro-2-(3-chloro-4-methoxy-phenylsulfonylamino)-N-(4-(morpholine-4-sulfonyl)-phenyl)-benzamide; M.p.: 274° C.

77) 5-Chloro-N-(4-(morpholine-4-sulfonyl)-phenyl)-2-(2,4,6-trimethyl-phenylsulfonylamino)-benzamide; M.p.: 240° C.

78) 5-Chloro-N-(4-(morpholine-4-sulfonyl)-phenyl)-2-(3-nitro-phenylsulfonylamino)-benzamide; M.p.: 220° C.

79) 5-Chloro-2-(4-methoxy-phenylsulfonylamino)-N-(4-(morpholine-4-sulfonyl)-phenyl)-benzamide; M.p.: 269° C.

80) 5-Chloro-N-(4-(morpholine-4-sulfonyl)-phenyl)-2-(3-trifluoromethyl-phenylsulfonylamino)-benzamide; M.p.: 212° C.

81) 2-(4-Bromo-2,5-dichloro-thiophene-3-sulfonylamino)-5-chloro-N-(4-(morpholine-4-sulfonyl)-phenyl)-benzamide; M.p.: 267° C.

82) 5-Chloro-N-(4-(morpholine-4-sulfonyl)-phenyl)-2-(2-trifluoromethyl-phenylsulfonylamino)-benzamide; M.p.: 234° C.

83) 5-Chloro-2-(3-chloro-phenylsulfonylamino)-N-(4-(morpholine-4-sulfonyl)-phenyl)-benzamide; M.p.: 206° C.

84) 2-(4-Bromo-2-methoxy-phenylsulfonylamino)-5-chloro-N-(4-(morpholine-4-sulfonyl)-phenyl)-benzamide; M.p.: 260° C.

85) 5-Chloro-2-(2,6-dichloro-phenylsulfonylamino)-N-(4-(morpholine-4-sulfonyl)-phenyl)-benzamide; M.p.: 244° C.

86) 5-Chloro-2-(2-cyano-phenylsulfonylamino)-N-(4-(morpholine-4-sulfonyl)-phenyl)-benzamide; M.p.: 200° C.

87) 2-(4-Butoxy-phenylsulfonylamino)-5-chloro-N-(4-(morpholine-4-sulfonyl)-phenyl)-benzamide; M.p.: 225° C.

88) 5-Chloro-2-(3-fluoro-phenylsulfonylamino)-N-(4-(morpholine-4-sulfonyl)-phenyl)-benzamide; M.p.: 204° C.

89) 2-(4-Chloro-phenylsulfonylamino)-N-(4-(morpholine-4-sulfonyl)-phenyl)-5-(morpholin-4-yl)-benzamide; M.p.: 264° C.

90) 2-(4-Chloro-phenylsulfonylamino)-4,5-dimethoxy-N-(4-(1,1-dioxo-thiomorpholine-4-sulfonyl)-phenyl)-benzamide and 91) 2-(4-Chloro-phenylsulfonylamino)-4,5-dimethoxy-N-(4-(1-oxo-thiomorpholine-4-sulfonyl)-phenyl)-benzamide 500 mg (0.82 mmol) of 2-(4-chloro-phenylsulfonylamino)-4,5-dimethoxy-N-(4-(thiomorpholine-4-sulfonyl)-phenyl)-benzamide in 50 ml of acetone were cooled to 0° C. A solution of 371 mg (1.23 mmol) of 57% m-chloroperbenzoic acid in 20 ml of acetone was added and the mixture was stirred at room temperature over night. For working up, it was poured onto water/ice and the precipitate was filtered off with suction. The two products obtained as a mixture were separated by chromatography over silica with methylene chloride/methanol (97:3).

Analogously were obtained:

92) 5-Chloro-2-(4-chloro-phenylsulfonylamino)-N-(4-(1,1-dioxo-thiomorpholine-4-sulfonyl)-phenyl)-benzamide; M.p.: 182° C.

93) 5-Chloro-2-(4-chloro-phenylsulfonylamino)-N-(4-(1-oxo-thiomorpholine-4-sulfonyl)-phenyl)-benzamide; M.p.: 233° C.

94) 5-Chloro-2-(5-chloro-thiophene-2-sulfonylamino)-N-(4-(morpholine-4-sulfonyl)-phenyl)-benzamide sodium salt A mixture of 0.48 g finely powdered sodium hydroxide and 7 g of 5-chloro-2-(5-chloro-thiophene-2-sulfonylamino)-N-(4-(morpholine-4-sulfonyl)-phenyl)-benzamide in 250 ml of ethanol was brought into solution by short heating. Then the mixture was evaporated in vacuo, 50 ml of water were added and it was again evaporated in vacuo to dryness. This procedure was repeated twice. The resulting product was dried in vacuo at 50° C. M.p.: 343° C. (Dec.)

Analogously to the above compounds the following example compounds were obtained:

95) 2-(5-Chloro-thiophene-2-sulfonylamino)-4,5-dimethoxy-N-(4-(N-methyl-N-(pyridin-3-yl-methyl)-aminosulfonyl)-phenyl)-benzamide hydrochloride; M.p.: 214° C.

96) 5-Chloro-2-(4-chloro-phenylsulfonylamino)-N-(4-(morpholine-4-sulfonyl)-3-methyl-phenyl)-benzamide; M.p.: 192° C.

97) 5-Chloro-2-(4-chloro-phenylsulfonylamino)-N-(4-(cis-2,6-dimethyl-morpholine-4-sulfonyl)-3-methyl-phenyl)-benzamide; M.p.: 254° C.

98) 5-Chloro-2-(4-chloro-phenylsulfonylamino)-N-(4-(3,5-dimethyl-piperidine-1-sulfonyl)-3-methyl-phenyl)-benzamide; M.p.: 242° C.

99) 5-Chloro-2-(4-chloro-phenylsulfonylamino)-N-(4-(piperidine-1-sulfonyl)-3-methyl-phenyl)-benzamide; M.p.: 189° C.

100) 4,5-Dimethoxy-2-(3,5-dimethyl-isoxazole-4-sulfonylamino)-N-(4-(N-methyl-N-(pyridin-3-yl-methyl)-aminosulfonyl)-phenyl)-benzamide; M.p.: 213° C.

101) 4,5-Dimethoxy-2-(3,5-dimethyl-isoxazole-4-sulfonylamino)-N-(4-(N-(pyridin-3-yl-methyl)-aminosulfonyl)-phenyl)-benzamide; M.p.: 216° C.

102) 5-Chloro-2-(2,4-dimethyl-thiazole-5-sulfonylamino)-N-(4-(morpholine-4-sulfonyl)-phenyl)-benzamide; M.p.: 190° C.

103) 2-(4-Chloro-phenylsulfonylamino)-4,5-dimethoxy-N-(4-(3,5-dimethyl-piperidine-1-sulfonyl)-phenyl)-benzamide; M.p.: 249° C. (Dec.)

104) 2-(4-Chloro-phenylsulfonylamino)-N-(4-(N-methyl-N-(pyridin-3-yl-methyl)-aminosulfonyl)-phenyl)-benzamide; Resin 105) 2-(4-Chloro-phenylsulfonylamino)-3,4-dimethoxy-N-(4-(N-methyl-N-(pyridin-3-yl-methyl)-aminosulfonyl)-phenyl)-benzamide; M.p.: 241° C.

106) 5-Bromo-2-(5-chloro-thiophene-2-sulfonylamino)-N-(4-(morpholine-4-sulfonyl)-3-methyl-phenyl)-benzamide; M.p.: 249° C.

107) 5-Bromo-2-(5-chloro-thiophene-2-sulfonylamino)-N-(4-(cis-2,6-dimethyl-morpholine-4-sulfonyl)-phenyl)-benzamide; M.p.: 244° C.

108) 5-Bromo-2-(5-chloro-thiophene-2-sulfonylamino)-N-(4-(thiomorpholine-4-sulfonyl)-phenyl)-benzamide; M.p.: 197° C.

109) 2-(5-chloro-thiophene-2-sulfonylamino)-4,5-dimethoxy-N-(4-(1,2,3,4-tetrahydro-isoquinoline-2-sulfonyl)-phenyl)-benzamide; M.p.: 213° C.

110) 2-(5-Chloro-thiophene-2-sulfonylamino)-4,5-dimethoxy-N-(4-(thiomorpholine-4-sulfonyl)-phenyl)-benzamide; M.p.: 232° C.

111) 2-(5-Chloro-thiophene-2-sulfonylamino)-4,5-dimethoxy-N-(4-(cis-2,6-dimethyl-piperidine-1-sulfonyl)-phenyl)-benzamide; M.p.: 213° C.
112) 5-Chloro-2-(3,5-dimethyl-isoxazole-4-sulfonylamino)-N-(4-(1,2,3,4-tetrahydro-isoquinoline-2-sulfonyl)-phenyl)-benzamide; M.p.: 260° C.
113) 5-Chloro-2-(3,5-dimethyl-isoxazole-4-sulfonylamino)-N-(4-(N-methyl-N-(pyridin-3-yl-methyl)-aminosulfonyl)-phenyl)-benzamide; M.p.: 65° C. (sintering)
114) 6-Methyl-2-(4-chloro-phenylsulfonylamino)-N-(4-(perhydroazepine-1-sulfonyl)-phenyl)-benzamide; M.p.: 151° C.
115) 6-Chloro-2-(4-chloro-phenylsulfonylamino)-N-(4-(pyrrolidine-1-sulfonyl)-phenyl)-benzamide; M.p.: 217° C.
116) 5-Chloro-2-(4-chloro-phenylsulfonylamino)-N-(4-(N-ethyl-N-(pyridin-4-yl-methyl)-aminosulfonyl)-phenyl)-benzamide; Resin
117) 2-(4-Chloro-phenylsulfonylamino)-N-(4-thiomorpholine-4-sulfonyl)-phenyl)-benzamide; M.p.: 209° C.
118) 3-Methyl-2-(4-chloro-phenylsulfonylamino)-N-(4-(N-methyl-N-(2-(pyridin-2-yl)-ethyl)-aminosulfonyl)-phenyl)-benzamide; M.p.: 193° C.
119) 5-Chloro-4-methoxy-2-(5-chloro-thiophene-2-sulfonylamino)-N-(4-(morpholine-4-sulfonyl)-phenyl)-benzamide; Oil
120) 5-Chloro-4-methoxy-2-(5-chloro-thiophene-2-sulfonylamino)-N-(4-(cis-2,6-dimethyl-morpholine-1-sulfonyl)-phenyl)-benzamide; M.p.: 89° C.
121) 5-Chloro-4-methoxy-2-(5-chloro-thiophene-2-sulfonylamino)-N-(4-(N-pyridin-3-yl)-N-methyl-aminosulfonyl)-phenyl)-benzamide; M.p.: 135° C.
122) 2-(4-Chloro-phenylsulfonylamino)-4,5-dimethoxy-N-(4-(cis-2,6-dimethyl-morpholine-4-sulfonyl)-phenyl)-benzamide sodium salt; M.p.: 330° C. (Dec)
123) 5-Chloro-2-(3,5-dimethyl-isoxazole-4-sulfonylamino)-N-(4-(cis-2,6-dimethyl-morpholine-4-sulfonyl)-phenyl)-benzamide; M.p.: 230° C.
124) 5-Chloro-2-(3,5-dimethyl-isoxazole-4-sulfonylamino)-N-(4-(3,5-dimethylpiperidine-1-sulfonyl)-phenyl)-benzamide; M.p.: 61° C.
125) 5-Chloro-2-(3,5-dimethyl-isoxazole-4-sulfonylamino)-N-(4-(morpholine-4-sulfonyl)-phenyl)-benzamide; M.p.: 286° C.
126) 4-Chloro-2-(4-chloro-phenylsulfonylamino)-N-(4-(cis-2,6-dimethyl-morpholine-4-sulfonyl)-phenyl)-benzamide; M.p.: 103° C.
127) 5-Chloro-2-(4-chloro-phenylsulfonylamino)-N-(3-methyl-4-(2,3-dihydro-1H-isoindol-2-sulfonyl)-phenyl)-benzamide
128) 5-Chloro-2-(3,5-dimethyl-isoxazole-4-sulfonylamino)-N-(4-(cis-2,6-dimethyl-morpholine-4-sulfonyl)-phenyl)-benzamide sodium salt; M.p.: 249° C.
129) 2-(4-Chloro-phenylsulfonylamino)-6-methyl-N-(4-(thiomorpholine-4-sulfonyl)-phenyl)-benzamide; M.p.: 189° C.
130) 2-(4-Chloro-phenylsulfonylamino)-6-methyl-N-(4-(pyridin-3-ylmethylamino-sulfonyl)-phenyl)-benzamide; M.p.: 219° C.
131) 6-Chloro-2-(4-chloro-phenylsulfonylamino)-N-(4-(thiomorpholine-4-sulfonyl)-phenyl)-benzamide; M.p.: 186° C.
132) 6-Chloro-2-(4-chloro-phenylsulfonylamino)-N-(4-(2,6-dimethyl-morpholine-4-sulfonyl)-phenyl)-benzamide; M.p.: 192° C.
133) 2-(4-Chloro-phenylsulfonylamino)-N-(4-benzylsulfamoyl-phenyl)-benzamide
134) 2-(4-Chloro-phenylsulfonylamino)-5-methoxy-N-(4-(thiomorpholine-4-sulfonyl)-phenyl)-benzamide; M.p.: 239° C.

Pharmaceutical Examples

A) Suspension for Oral Administration

A vehicle suspension (designated below as vehicle MC/T80) was prepared by adding 5 g of methyl cellulose and 5 ml of Tween® 80 to 1 l of doubly distilled water and stirring the mixture overnight. For preparing an aqueous suspension which comprises 3 mg/ml of 5-chloro-2-(5-chloro-thiophene-2-sulfonylamino)-N-(4-(morpholine-4-sulfonyl)-phenyl)-benzamide sodium salt, 15 mg of the compound of example 94 were added to 5 ml of vehicle MC/T80 and the mixture was stirred for 15 min.

Analogously, by adding 5 mg, 1.5 mg and 0.5 mg, of the compound of example 94 to 5 ml each of vehicle MC/T80, suspensions for oral administration were prepared with comprise 1 mg/ml, 0.3 mg/ml and 0.1 mg/ml, respectively, of 5-chloro-2-(5-chloro-thiophene-2-sulfonylamino)-N-(4-(morpholine-4-sulfonyl)-phenyl)-benzamide sodium salt.

Pharmacological Tests

Test 1) Anti-Hyperalgesic Effect in the Carrageenan Model of Inflammatory Triggered Thermal Hyperalgesia in Mice after Oral Administration In this in vivo model the anti-hyperalgesic effect was determined in mice in which a thermal hyperalgesia of the hind paws had been induced by injection of carrageenan, by measuring the paw withdrawal latency (PWL), i.e. the time until the mouse withdrew its hind paw from a heated spot of the ground. These experiments and all other animal experiments were performed in accordance with animal protection law and guidelines for the use of experimental animals.

Three test groups and one control group of animals were used each consisting of three male C57B6 mice. 1 h before injection of carrageenan, either the test compound or vehicle was administered to the animals orally by gavage. In the test groups, mice received 100 µl/10 g body weight of a suspension of the test compound in vehicle MC/T80 comprising 0.1 mg/ml, 0.3 mg/ml or 1 mg/ml (prepared as described in pharmaceutical example A) for attaining a dosage of 1 mg/kg body weight, 3 mg/kg body weight and 10 mg/kg body weight, respectively. In the control group, mice analogously received 100 µl/10 g body weight of vehicle MC/T80. For induction of hind paw inflammatory pain, then in all groups carrageenan (Sigma, Deisenhofen, Germany) at a concentration of 2% in 10 µl of saline was injected into the plantar aspect of both hind paws of the mice under slight general isofluran anesthesia. 1 h before injection of carrageenan, i.e. immediately before administration of the test compound or vehicle, and 1 h, 2 h, 4 h and 6 h after injection of carrageenan, thermal hyperalgesia was determined.

Thermal hyperalgesia was determined by measuring the paw withdrawal latency (PWL) by means of the automatic plantar test, first described for rats in K. Hargreaves et al., Pain 32 (1988), 77-88, and used in an adapted version fitted to mice described in H. Gühring et al., J. Neurosci. 20 (2000), 6714-6720. To restrict animal movement, 10.5×13.0×4.5 cm test cages were used. Instead of a glass floor, a metal grid bottom was used. PWL (in seconds) was determined on exposure of the paw to a defined thermal stimulus using a commercially available apparatus (Plantar Test, Ugo Basile Biological Research Apparatus, Comerio, Italy) fitted with a mini camera to ensure proper placement of the infrared heat below the hind paw of interest. The timer which measured the duration of reflected infrared light by the hind paw was started by the investigator and stopped once the animal shook the affected paw. A cut-off was set at 16 seconds to prevent tissue damage. For each hind paw and each time point, the mean of three to four PWL measurements was determined.

Table 1 contains the PWL values obtained in test 1 with the compound of example 94. The given PWL values (in seconds) are the mean±SEM (standard error of the mean) of the PWL values obtained for each hind paw of each animal (N (number of paws)=6) of the indicated dosage group at the time points 1 h, 2 h, 4 h and 6 h after injection of carrageenan, as well as the baseline PWL values (BL) determined 1 h before administration of the test compound or vehicle and injection of carrageenan.

TABLE 1

Mean PWL values ± SEM (in seconds) obtained in test 1 with the compound of example 94

| Dosage (mg/kg body weight) | N | BL | Time | | | |
|---|---|---|---|---|---|---|
| | | | 1 h | 2 h | 4 h | 6 h |
| 0 (Control) | 6 | 10.93 ± 0.37 | 3.10 ± 0.33 | 2.88 ± 0.40 | 3.00 ± 0.25 | 2.92 ± 0.51 |
| 1 | 6 | 11.08 ± 0.40 | 4.08 ± 0.62 | 3.80 ± 0.28 | 3.98 ± 0.79 | 3.86 ± 0.48 |
| 3 | 6 | 10.69 ± 0.27 | 8.42 ± 0.53 | 10.16 ± 0.33 | 10.84 ± 0.63 | 3.74 ± 0.47 |
| 10 | 6 | 10.97 ± 0.40 | 12.46 ± 0.91 | 11.24 ± 0.77 | 11.11 ± 0.54 | 3.40 ± 0.46 |

In FIG. 1 the time course of the mean PWL values obtained in test 1 with the compound of example 94 is depicted (Y-axis: paw withdrawal latency (PWL) in seconds; X-axis: time in hours after injection of carrageenan; BL: determination of baseline value before injection of carrageenan; ♦-♦: 0 mg/kg body weight (control); ●-●: 1 mg/kg body weight; ■-■: 3 mg/kg body weight; ▲-▲: 10 mg/kg body weight).

For the statistical analysis, PWL values were used in two ways, first with a 2-way ANOVA test based on the PWL values and second with a 1-way ANOVA test based on the area under the curve (AUC) values for the time period of 6 h after injection of carrageenan. A repeated measures 2-way ANOVA test (factor treatment and repeated measures factor time) was performed on PWL measurements. In case the interaction (treatment×time) was statistically significant, a Winer complementary analysis was done to investigate the effect of treatment for each time point. A Dunnett's test was used to study the potential differences between the control group and the test groups. Statistically significant anti-hyperalgesic effects were observed at a dosage of 3 mg/kg body weight and a dosage of 10 mg/kg body weight of the compound of example 94 from 1 h to 4 h after carrageenan injection.

As a quantitative measure of the efficacy of a test compound over an extended time period, the area under the curve (AUC) of the PWL values for the time period from 1 h to 6 h after injection of carrageenan (AUC1 h-6 h) was determined for each paw (N=6) for the test groups and compared with the AUC1 h-6 h value of the PWL values of the control group (N=6). For statistical analysis, a 1-way ANOVA test was applied on individual AUC1 h-6 h values followed by a Dunnett's test for comparison of the test groups with the control group. Table 2 contains the mean±SEM of the individual AUC1 h-6 h values of the PWL values obtained in test 1 with the compound of example 94.

TABLE 2

Mean of individual AUC1h-6h values of PWL values obtained in test 1 with the compound of example 94, and statistical findings

| Dosage (mg/kg body weight) | N | AUC1h-6h of PWL (mean ± SEM) | Statistical evaluation vs. control (1) |
|---|---|---|---|
| 0 (Control) | 6 | 14.80 ± 1.22 | — |
| 1 | 6 | 19.57 ± 2.19 | ns |
| 3 | 6 | 44.87 ± 1.21 | *** |
| 10 | 6 | 48.70 ± 2.06 | *** |

(1) ns: not significant; ***: significant, p < 0.0001 (ANOVA & Dunnett)

The results shown in Tables 1 and 2 and FIG. 1 demonstrate that the compounds of the invention substantially reduce or even completely reverse thermal hyperalgesia during at least fours hours after a single oral administration and have a pronounced anti-hyperalgesic and thus analgesic effect.

Test 2) Anti-Allodynic Effect in the Spared Nerve Injury (SNI) Model of Neuropathic Pain in Mice after Oral Administration In this in vivo mouse model of chronic neuropathic pain the effect on tactile allodynia, a painful sensation after a normally not painful mechanical stimulus, which had been induced in a hind paw by surgical lesion of the sciatic nerve, was determined by measuring the paw withdrawal threshold (PWT), i.e. the exerted force (expressed in grams) at which the mouse withdrew its hind paw.

Tactile allodynia was determined at both hind paws, i.e. ipsilateral and contralateral to the lesion if determined subsequent to surgery, with the automatic von Frey test in which the plantar skin of the hind paws was exposed to a pressure stimulus of increasing intensity up to 5 grams using a dump needle stick. The force in grams at which the animal responded withdrawal of the hind paw (paw withdrawal threshold, PWT), was used as a measure of tactile allodynia.

Two test groups and one control group of animals were used each consisting of four male C57B6 mice. In all groups, baseline PWT values (BL) were determined before surgery. For induction of neuropathic pain then, under general anesthesia, in all groups the two major branches of the sciatic nerve were ligated and transected, with the sural nerve left intact (spared nerve injury, SNI). In this model of neuropathic pain, tactile allodynia developed completely within two days after nerve transection in the hind paw ipsilateral to the lesion and remained stable in the control group over the complete observation period of the experiment.

7 days after surgery, immediately before administration of the test compound, i.e. at the time 0 h, in all groups PWT values were determined for the injured ipsilateral hind paw and the non-injured contralateral hind paw. Then either the test compound or vehicle was administered to the animals orally by gavage. In the test groups, mice received 100 μl/10 g body weight of a suspension of the test compound in vehicle MC/T80 comprising 0.3 mg/ml or 3 mg/ml (prepared as described in pharmaceutical example A) for attaining a dosage of 3 mg/kg body weight and 30 mg/kg body weight, respectively. In the control group, mice analogously received 100 μl/10 g body weight of vehicle MC/T80. 1 h, 2 h, 4 h and 6 h after administration, PWT values were determined.

Table 3 contains the PWT values obtained in test 2 with the compound of example 94. The given PWT values (in grams) are the mean±SEM (standard error of the mean) of the PWT measurements performed with the ipsilateral hind paw and the contralateral hind paw, respectively, of each animal of the indicated group (N (number of animals)=4) at the time points 0 h (i.e. before administration of test compound or vehicle) and 1 h, 2 h, 4 h and 6 h after administration of test compound or vehicle, as well as the baseline PWT values (BL) determined before surgery.

(mean±SEM) obtained for the compound of example 94 are given in Table 4. Statistical analysis was performed with a 1-way ANOVA test based on the DeltaAUC1 h-6 h values. Both dosages of the compound of example 94, 3 mg/kg body weight and 30 mg/kg body weight, achieved significant improvement over the control group treated with vehicle only.

TABLE 4

Mean DeltaAUC1h-6h values of PWT values obtained in test 2 with the compound of example 94, and statistical findings

| Dosage (mg/kg body weight) | N | DeltaAUC1h-6h of PWL (mean ± SEM) | Statistical evaluation vs. control (1) |
|---|---|---|---|
| 0 (Control) | 4 | 14.22 ± 0.80 | — |

TABLE 3

Mean PWT values ± SEM (in grams) obtained in test 2 with the compound of example 94

| Dosage (mg/kg body weight) | BL | Injured ipsilateral paw Time | | | | | Non-injured contralateral paw Time | | | | |
|---|---|---|---|---|---|---|---|---|---|---|---|
| | | 0 h | 1 h | 2 h | 4 h | 6 h | 0 h | 1 h | 2 h | 4 h | 6 h |
| 0 (Control) | 4.63 ± 0.14 | 1.69 ± 0.14 | 1.88 ± 0.08 | 1.84 ± 0.14 | 1.65 ± 0.14 | 1.88 ± 0.22 | 4.47 ± 0.21 | 4.78 ± 0.14 | 4.69 ± 0.10 | 4.55 ± 0.13 | 4.58 ± 0.12 |
| 3 | 4.75 ± 0.14 | 1.58 ± 0.11 | 2.96 ± 0.10 | 4.64 ± 0.11 | 4.12 ± 0.17 | 2.50 ± 0.40 | 4.84 ± 0.11 | 4.66 ± 0.14 | 4.95 ± 0.02 | 4.61 ± 0.13 | 4.82 ± 0.13 |
| 30 | 4.70 ± 0.18 | 1.91 ± 0.12 | 3.70 ± 0.46 | 4.66 ± 0.10 | 4.51 ± 0.17 | 4.24 ± 0.08 | 4.69 ± 0.23 | 4.82 ± 0.10 | 4.84 ± 0.10 | 4.70 ± 0.19 | 4.55 ± 0.12 |

In FIG. 2 the time course of the mean PWT values obtained in test 2 with the compound of example 94 is depicted (Y-axis: paw withdrawal threshold (PWT) in grams; X-axis: time in hours after administration of test compound or vehicle; BL: determination of baseline value before surgery; il: injured ipsilateral paw; cl: non-injured contralateral paw; ♦-♦: 0 mg/kg body weight il (control); ●-●: 3 mg/kg body weight il; ■-■: 30 mg/kg body weight il; ◇-◇: 0 mg/kg body weight cl (control); ○-○: 3 mg/kg body weight cl; □-□: 30 mg/kg body weight cl).

For the statistical analysis, PWT values were used in two ways, first with a 2-way ANOVA test based on the PWT values and second with a 1-way ANOVA test based on area under the curve (AUC) values for the time period of 6 h after application of the test compound or vehicle. A repeated measures 2-way ANOVA test (factor treatment and repeated measures factor time) was performed on PWT measurements. In case the interaction (treatment×time) was statistically significant, a Winer complementary analysis was done to investigate the effect of treatment for each time point. A Dunnett's test was used to study the potential differences between the control group and the test groups. Statistically significant antallodynic effects were observed at a dosage of 3 mg/kg body weight from 1 h to 4 h and at a dosage of 30 mg/kg body weight from 1 h to 6 h after administration of the compound of example 94.

As a quantitative measure of the efficacy of a test compound over an extended time period, the area under the curve (AUC) of the individual PWT values for the time period from 1 h to 6 h after administration of test compound or vehicle (AUC1 h-6 h) was determined for the ipsilateral paws of each group and the obtained value subtracted from the value determined for the contralateral paws of the same group to give DeltaAUC1 h-6 h values for each group. The results TABLE 4-continued Mean DeltaAUC1h-6h values of PWT values obtained in test 2 with the compound of example 94, and statistical findings

| Dosage (mg/kg body weight) | N | DeltaAUC1h-6h of PWL (mean ± SEM) | Statistical evaluation vs. control (1) |
|---|---|---|---|
| 3 | 4 | 4.60 ± 1.20 | *** |
| 30 | 4 | 1.52 ± 0.94 | *** |

(1) ***: significant, p < 0.0001 (ANOVA & Dunnett)

The results shown in Tables 3 and 4 and FIG. 2 demonstrate the substantial reduction or even complete reversion of tactical allodynia during at least fours hours after a single oral administration and thus the utility of the compounds of the invention for treating various types of pain.

BRIEF DESCRIPTION OF DRAWINGS

FIG. 2 shows the time course of the mean paw withdrawal threshold (PWT) obtained in pharmacological test 2 with the compound of example 94.

Figure 1:
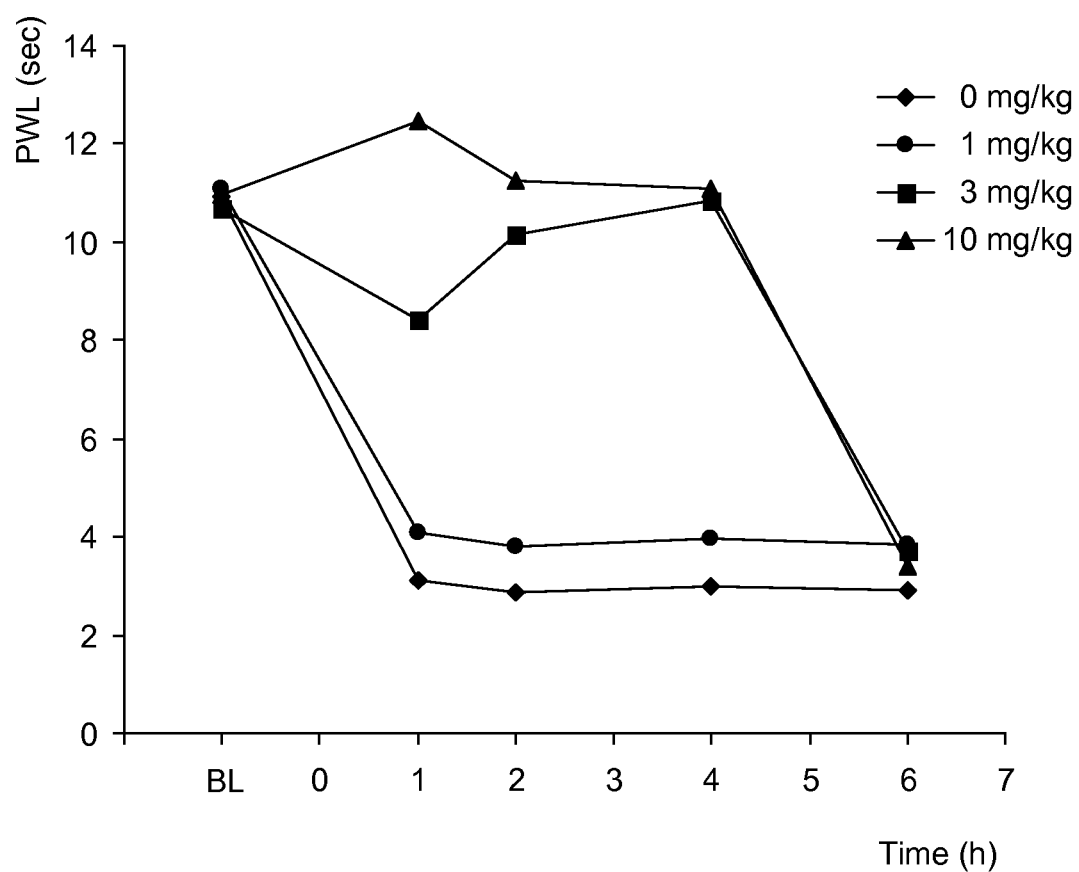
FIG. 1 shows the time course of the mean paw withdrawal latency (PWL) obtained in pharmacological test 1 with the compound of example 94.

What is claimed is:

1. A method of treating pain, comprising: administering to a patient in need thereof, a pharmaceutically effective amount of a compound of the formula I,

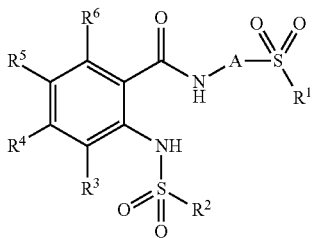

wherein
A is phenylene which can be substituted by one or more identical or different substituents chosen from halogen, $(C_1\text{-}C_4)$-alkyl and trifluoromethyl;
$R^1$ is chosen from $R^7R^8N$ and Het;
$R^2$ is phenyl or heteroaryl which can both be substituted by one or more identical or different substituents chosen from halogen, $(C_1\text{-}C_4)$-alkyl, trifluoromethyl, trifluoromethoxy, nitro, cyano, $(C_1\text{-}C_4)$-alkyl-O—, $(C_1\text{-}C_4)$-alkyl-CO—NH— and $(C_1\text{-}C_4)$-alkyl-S(O)$_2$—;
$R^3$, $R^4$, $R^5$ and $R^6$, which are independent of each other and can be identical or different, are chosen from hydrogen, halogen, $(C_1\text{-}C_4)$-alkyl, trifluoromethyl, cyano and $(C_1\text{-}C_4)$-alkyl-O—;
$R^7$ is chosen from hydrogen, $(C_1\text{-}C_4)$-alkyl and $(C_3\text{-}C_5)$-alkenyl;
$R^8$ is chosen from $(C_1\text{-}C_4)$-alkyl, $(C_1\text{-}C_4)$-alkyl-O—$(C_1\text{-}C_4)$-alkyl-, di($(C_1\text{-}C_4)$-alkyl)N—$(C_1\text{-}C_4)$-alkyl-, $(C_3\text{-}C_5)$-alkenyl, $(C_3\text{-}C_7)$-cycloalkyl, $(C_3\text{-}C_7)$-cycloalkyl-$(C_1\text{-}C_4)$-alkyl-, phenyl-$(C_1\text{-}C_4)$-alkyl-, indanyl and pyridinyl-$(C_1\text{-}C_4)$-alkyl-, wherein cycloalkyl and pyridinyl can be substituted by one or more identical or different $(C_1\text{-}C_4)$-alkyl substituents;
heteroaryl is a residue of a monocyclic 5-membered or 6-membered aromatic heterocycle which contains one or two identical or different ring heteroatoms chosen from nitrogen, oxygen and sulfur;
Het is a residue of a monocyclic 5-membered, 6-membered or 7-membered saturated or partially unsaturated heterocycle which contains a ring nitrogen atom via which the group Het is bonded to the group -A-S(O)$_2$—, and which can contain one further ring heteroatom chosen from nitrogen, oxygen and sulfur wherein the sulfur atom can carry one or two oxo groups, and which can be substituted by one or more identical or different $(C_1\text{-}C_4)$-alkyl substituents, and to which a benzene ring can be fused wherein the benzene ring can be substituted by one or more identical or different substituents chosen from halogen, $(C_1\text{-}C_4)$-alkyl and trifluoromethyl;
in any of its stereoisomeric forms, or a mixture of stereoisomeric forms in any ratio, or a physiologically acceptable salt thereof.

2. The method according to claim 1, wherein
A is 1,4-phenylene which can be substituted by one or two identical or different substituents chosen from halogen and $(C_1\text{-}C_4)$-alkyl;
$R^1$ is Het;
Het is a residue of a monocyclic 5-membered, 6-membered or 7-membered heterocycle which is saturated and contains a ring nitrogen atom via which the group Het is bonded to the group -A-S(O)$_2$—, and which can contain one further ring heteroatom chosen from nitrogen, oxygen and sulfur wherein the sulfur atom can carry one or two oxo groups, and which can be substituted by one or more identical or different $(C_1\text{-}C_4)$-alkyl substituents;
in any of its stereoisomeric forms, or a mixture of stereoisomeric forms in any ratio, or a physiologically acceptable salt thereof.

3. The method according claim 1, wherein
$R^2$ is phenyl or heteroaryl which can both be substituted by one, two or three identical or different substituents chosen from halogen, $(C_1\text{-}C_4)$-alkyl and trifluoromethyl;
two of the groups $R^3$, $R^4$, $R^5$ and $R^6$ are hydrogen and the others of the groups $R^3$, $R^4$, $R^5$ and $R^6$, which are independent of each other and can be identical or different, are chosen from hydrogen, halogen, $(C_1\text{-}C_4)$-alkyl and $(C_1\text{-}C_4)$-alkyl-O—;
heteroaryl is a residue of a monocyclic 5-membered aromatic heterocycle which comprises one ring heteroatom chosen from nitrogen, oxygen and sulfur or two ring heteroatoms one of which is a nitrogen atom and the other of which is chosen from nitrogen, oxygen and sulfur;
in any of its stereoisomeric forms, or a mixture of stereoisomeric forms in any ratio, or a physiologically acceptable salt thereof.

4. The method according to claim 1, wherein
A is unsubstituted 1,4-phenylene;
$R^1$ is Het;
$R^2$ is phenyl or heteroaryl which can both be substituted by one, two or three identical or different substituents chosen from halogen and $(C_1\text{-}C_4)$-alkyl;
$R^3$ and $R^6$ are hydrogen, $R^4$ is chosen from hydrogen, halogen and $(C_1\text{-}C_4)$-alkyl-O—, and $R^5$ is chosen from halogen and $(C_1\text{-}C_4)$-alkyl-O—;
heteroaryl is chosen from thiophenyl and a residue of a 5-membered aromatic heterocycle which comprises a ring nitrogen atom and one further ring heteroatom chosen from nitrogen, oxygen and sulfur;
Het is a residue of a monocyclic 6-membered saturated heterocycle which contains a ring nitrogen atom via which the group Het is bonded to the group -A-S(O)$_2$—, and which can contain one further ring heteroatom chosen from oxygen and sulfur wherein the sulfur atom can carry one or two oxo groups, and which can be substituted by one, two, three or four identical or different $(C_1\text{-}C_4)$-alkyl substituents;
in any of its stereoisomeric forms, or a mixture of stereoisomeric forms in any ratio, or a physiologically acceptable salt thereof.

5. The method according to claim 1, wherein the compound of the formula I is selected from:
2-(4-chloro-phenylsulfonylamino)-4,5-dimethoxy-N-(4-(thiomorpholine-4-sulfonyl)-phenyl)-benzamide,
2-(4-chloro-phenylsulfonylamino)-N-(4-(cis-2,6-dimethyl-morpholine-4-sulfonyl)-phenyl)-4,5-dimethoxy-benzamide,
5-chloro-2-(5-chloro-thiophene-2-sulfonylamino)-N-(4-(morpholine-4-sulfonyl)-phenyl)-benzamide, and
5-chloro-2-(3,5-dimethyl-isoxazole-4-sulfonylamino)-N-(4-(cis-2,6-dimethyl-morpholine-4-sulfonyl)-phenyl)-benzamide,
or a physiologically acceptable salt thereof.

6. The method according to claim 1, wherein the pain is selected from: pain associated with a chronic musculoskeletal disease, pain associated with menstrual bleeding, pain associated with a joint disease, inflammatory pain, pain associated with multiple sclerosis, pain associated with neuritis, pain associated with a carcinoma, pain associated with a sarcoma, pain associated with AIDS, pain associated with chemotherapy, amputation pain, trigeminus neuralgia, headache, neuropathic pain, pain following an injury, post-operative pain, pain associated with an attack of gout, toothache, pain associated with a jaw-bone surgery intervention and acute herpes zoster pain.

7. The method according to claim 6, wherein the pain is selected from: pain associated with a joint disease, inflammatory pain and neuropathic pain.

8. The method according to claim 1, wherein the pain is selected from: pain associated with osteoarthritis or pain associated with rheumatoid arthritis.

9. The method according to claim 1, wherein the pain is selected from: pain associated with intestinal inflammation or pain associated with cardiac muscle inflammation.

10. The method according to claim 1, wherein the pain is selected from: post-herpes zoster neuralgia, neuropathic pain caused by metabolic dysfunctions, neuropathic pain associated with diabetic polyneuropathy, neuropathic pain following a surgical intervention or chemotherapy-induced neuropathic pain.

11. A method of treating pain, comprising: administering to a patient in need thereof, a pharmaceutically effective amount of an activator or stimulator of soluble guanylate cyclase of formula I of claim 1.

12. The method according to claim 11, wherein the pain is selected from: pain associated with a chronic musculoskeletal disease, pain associated with menstrual bleeding, pain associated with a joint disease, inflammatory pain, pain associated with multiple sclerosis, pain associated with neuritis, pain associated with a carcinoma, pain associated with a sarcoma, pain associated with AIDS, pain associated with chemotherapy, amputation pain, trigeminus neuralgia, headache, neuropathic pain, pain following an injury, post-operative pain, pain associated with an attack of gout, toothache, pain associated with a jaw-bone surgery intervention, and acute herpes zoster pain.

13. The method according to claim 11, wherein the pain is selected from: pain associated with a joint disease, inflammatory pain or neuropathic pain.

\* \* \* \* \*